United States Patent
Xu et al.

(10) Patent No.: US 9,044,514 B2
(45) Date of Patent: Jun. 2, 2015

(54) LIPID-PEPTIDE-POLYMER CONJUGATES AND NANOPARTICLES THEREOF

(75) Inventors: Ting Xu, Berkeley, CA (US); He Dong, Albany, CA (US); Jessica Shu, San Francisco, CA (US)

(73) Assignee: REGENTS OF THE UNIVERSITY OF CALIFORNIA, Oakland, CA (US)

( * ) Notice: Subject to any disclaimer, the term of this patent is extended or adjusted under 35 U.S.C. 154(b) by 0 days.

(21) Appl. No.: 13/610,637

(22) Filed: Sep. 11, 2012

(65) Prior Publication Data

US 2013/0121917 A1 May 16, 2013

Related U.S. Application Data

(63) Continuation-in-part of application No. PCT/US2011/028198, filed on Mar. 11, 2011.

(60) Provisional application No. 61/313,522, filed on Mar. 12, 2010.

(51) Int. Cl.
*A61K 47/42* (2006.01)
*A61K 47/48* (2006.01)
*B82Y 5/00* (2011.01)

(52) U.S. Cl.
CPC ............ *A61K 47/42* (2013.01); *A61K 47/48038* (2013.01); *A61K 47/48215* (2013.01); *A61K 47/488* (2013.01); *B82Y 5/00* (2013.01); *Y10S 977/773* (2013.01); *Y10S 977/906* (2013.01)

(58) Field of Classification Search
None
See application file for complete search history.

(56) References Cited

U.S. PATENT DOCUMENTS

| 7,452,679 B2 | 11/2008 | Stupp et al. |
| 2008/0299205 A1 | 12/2008 | Mayer et al. |
| 2010/0015173 A1 | 1/2010 | Boato et al. |

OTHER PUBLICATIONS

Matsuzaki, Katsum; "Magainins as paradigm for the mode of action of pore forming polypeptides." Biochim. Biophys. Acta (1998) 1376 p. 391-400.*
Nilsson, Per Gunnar and Lindman, Bjorn; "Water self diffusion in nonionic surfactant solutions. Hydrationand obstruction effects." J. Phys. Chem. (1983) 87 p. 4756-4761.*
Hiemenz , Paul; "Principles of colloid and surface chemistry" 1986, ISBN 0-8247-7476-0, table 8.1, p. 432.*
Ogihara, Nancy L. et al; "The crystal strucutre of the designed trimeric coiled coil coil-VaLd: Implications for engineering crystals and supramolecular assemblies." Protein Sci. (1997) 6 p. 80-88.*
Shu, Jessica Y et al; "New design of helix bundle peptide-polymer conjugates." Biomacromolecules (2008) 9 p. 2111-2117.*
Creighton, Thomas E.; "Stability of alpha-helixes." Nature (1987) 326 p. 547-548.*
Berendsen, Herman J. C.; "A glimpse of the holy grail?" Science (1998) 282(5389) p. 642-643.*
Chen, Yee-Hsiung et al; "Determination of the secondary structures of proteins by circular dichroism and optical rotation dispersion." Biochemistry (1972) 11(22) p. 4120-4131.*
Cannon, John B.; "Pharmaceutics and drug delivery aspects of heme and porphyrin therapy." J. Pharma. Sci. (1993) 82(5) p. 435-446.*
International Search Report and Written Opinion dated Oct. 18, 2011, issued in International Patent Application No. PCT/US11/28198, filed Mar. 11, 2011.
Shu et al., "New Design of Helix Bundle Peptide-Polymer Conjugates," 2008, Biomacromolecules, 9, pp. 2111-2117.

* cited by examiner

*Primary Examiner* — Maury Audet
*Assistant Examiner* — Fred Reynolds
(74) *Attorney, Agent, or Firm* — Kilpatrick Townsend & Stockton LLP

(57) ABSTRACT

The present invention provides a conjugate having a peptide with from about 10 to about 100 amino acids, wherein the peptide adopts a helical structure. The conjugate also includes a first polymer covalently linked to the peptide, and a hydrophobic moiety covalently linked to the N-terminus of the peptide, wherein the hydrophobic moiety comprises a second polymer or a lipid moiety. The present invention also provides helix bundles form by self-assembling the conjugates, and particles formed by self-assembling the helix bundles. Methods of preparing the helix bundles and particles are also provided.

15 Claims, 35 Drawing Sheets

A.

B.

A.

B.

A.

B.

C.

A.

B.

A.

B.

A.

B.

A.

B.

A.

B.

A.

B.

A.

B.

A.

B.

A.

B.

A.

B.

(A)

(B)

SEQUENCE LISTING

<160> NUMBER OF SEQ ID NOS: 5

<210> SEQ ID NO 1
<211> LENGTH: 30
<212> TYPE: PRT
<213> ORGANISM: Artificial Sequence

```
<220> FEATURE:
<223> OTHER INFORMATION: synthetic helical coiled-coil peptide 1CW

<400> SEQUENCE: 1

Glu Val Glu Ala Leu Glu Lys Lys Val Ala Ala Leu Glu Cys Lys Val
1               5                   10                  15

Gln Ala Leu Glu Lys Lys Val Glu Ala Leu Glu His Gly Trp
            20                  25                  30

<210> SEQ ID NO 2
<211> LENGTH: 30
<212> TYPE: PRT
<213> ORGANISM: Artificial Sequence
<220> FEATURE:
<223> OTHER INFORMATION: synthetic helical coiled-coil 4-helix bundle
      heme-binding peptide BB

<400> SEQUENCE: 2

Gly Gly Gly Glu Ile Trp Lys Leu His Glu Glu Phe Leu Cys Lys Phe
1               5                   10                  15

Glu Glu Leu Leu Lys Leu His Glu Glu Arg Leu Lys Lys Met
            20                  25                  30

<210> SEQ ID NO 3
<211> LENGTH: 12
<212> TYPE: PRT
<213> ORGANISM: Artificial Sequence
<220> FEATURE:
<223> OTHER INFORMATION: synthetic C-terminal peptide GB

<400> SEQUENCE: 3

Ala Tyr Ser Ser Gly Ala Pro Pro Met Pro Pro Phe
1               5                   10

<210> SEQ ID NO 4
<211> LENGTH: 30
<212> TYPE: PRT
<213> ORGANISM: Artificial Sequence
<220> FEATURE:
<223> OTHER INFORMATION: synthetic random coil peptide SR

<400> SEQUENCE: 4

Glu Gly Lys Ala Gly Glu Lys Ala Gly Ala Ala Leu Lys Cys Gly Val
1               5                   10                  15

Gln Glu Leu Glu Lys Gly Ala Glu Ala Gly Gly Gly Trp
            20                  25                  30

<210> SEQ ID NO 5
<211> LENGTH: 30
<212> TYPE: PRT
<213> ORGANISM: Artificial Sequence
<220> FEATURE:
<223> OTHER INFORMATION: synthetic helical coiled-coil peptide 1coi-W

<400> SEQUENCE: 5

Glu Val Glu Ala Leu Glu Lys Lys Val Ala Ala Leu Glu Ser Lys Val
1               5                   10                  15

Gln Ala Leu Glu Lys Lys Val Glu Ala Leu Glu His Gly Trp
            20                  25                  30
```

US 9,044,514 B2

LIPID-PEPTIDE-POLYMER CONJUGATES AND NANOPARTICLES THEREOF

CROSS-REFERENCES TO RELATED APPLICATIONS

This application is a continuation-in-part of PCT Application No. PCT/US11/28198, filed Mar. 11, 2011, which claims priority to U.S. Provisional Application No. 61/313,522, filed Mar. 12, 2010, which is incorporated in its entirety herein for all purposes.

STATEMENT AS TO THE RIGHTS TO THE INVENTION MADE UNDER FEDERALLY SPONSORED RESEARCH AND DEVELOPMENT

The invention described and claimed herein was made in part utilizing funds supplied by the U.S. Department of Energy under Contract No. DE-AC02-05CH11231 and under Grant No. KC202010, awarded by the Department of Energy-BES. The government has certain rights in this invention.

REFERENCE TO A SEQUENCE LISTING

This application includes a Sequence Listing as a text file named "SEQTXT_77429_850121_007711US.txt" created Sep. 10, 2012 and containing 2,207 bytes. The material contained in this text file is incorporated by reference.

BACKGROUND OF THE INVENTION

Synthetic nanoparticles based on peptides/proteins, lipids and polymers offer great promise for biomedical and pharmaceutical applications, such as drug delivery, new vaccine formulations, tissue engineering and protein therapeutics. They are also highly desirable for the food and cosmetic industries. Various approaches have been developed to prepare nanoparticles with different levels of success such as liposomes, dendrimers, crosslinked polymeric nanoparticles, polymersomes and synthetic virus-like nanoparticles using recombinant proteins. The polymeric approach tends to give large particles and there are limited reports to produce particles with sizes around 10-20 nm. As the major carrier for many therapeutic systems, liposomes can form nanoparticles with a wide range of sizes down to 20-30 nm and are commonly used for drug and gene delivery as well as skin cosmetics care and food industry. The liposome formation process is not instantaneous and typically involves multi-step procedures such as sonication, extrusion etc. Yet, the liposomes tend to form large aggregates and require optimization in particle size, polydispersity and shelf-life time. Synthetic virus-like nanoparticles, such as Inflexal V®, can be made using recombinant proteins that self-assemble into 20-100 nm diameter nanoparticles capable of displaying multiple antigenic peptides on their surface. However, extensive purification is required to remove residual compounds to avoid immune responses. In addition, they require refrigeration to prevent protein denaturation. Both limitations result in high cost and prevent their extensive utilization. Thus, it still remains a significant challenge to prepare monodisperse nanoparticles with diameters in the range of tens of nanometers that are stable at room temperature at low cost. Surprisingly, the present invention meets this and other needs.

BRIEF SUMMARY OF THE INVENTION

In some embodiments, the present invention provides a conjugate having a peptide with from about 10 to about 100 amino acids, wherein the peptide adopts a helical structure. The conjugate also includes a first polymer covalently linked to the peptide, and a hydrophobic moiety covalently linked to the N-terminus of the peptide, wherein the hydrophobic moiety comprises a second polymer or a lipid moiety.

In some embodiments, the present invention provides a helix bundle having from 2 to 6 conjugates of the present invention.

In some embodiments, the present invention provides a particle having from about 20 to about 200 conjugates of the present invention.

In some embodiments, the present invention provides a method of forming particles of the present invention by contacting a plurality of conjugates of the present invention such that the conjugates self-assemble to form the particles of the present invention.

In some embodiments, the present invention further provides a method for delivering a diagnostic or therapeutic agent to a subject comprising administering a particle to the subject. Thus, the particle includes from about 20 to about 200 conjugates of the present invention and the therapeutic agent.

BRIEF DESCRIPTION OF THE DRAWINGS

FIG. 19A shows the small angle x-ray scattering of particles prepared from the dC16-1CW-P2K-HHH conjugate 1 at 5 mg/ml in 25 mM phosphate buffer. Fitting of the data (solid line) to a core-shell spherical form factor yields a core diameter of ~3.8 nm, a shell thickness of ~5.7 nm, and polydispersity of ~7%. FIG. 19B is a vitreous ice cryogenic TEM of particles prepared from the dC16-1CW-P2K-HHH conjugate 1 at 1 mg/ml in 25 mM phosphate buffer at pH 7.5. FIG. 19C shows a negatively stained TEM of particles prepared from the dC16-1CW-P2K-HHH conjugate 1 at 1 mg/ml in 25 mM phosphate buffer at pH 7.5. FIG. 19D shows the sedimentation equilibrium analysis of particles prepared from the dC16-1CW-P2K conjugate 16 at 100 µM in 25 mM phosphate buffer. Fitting of the data (solid line) into a single-species model yields MW of 512 kDa corresponding to 26 trimolecular subunits.

FIG. 20A shows the concentration dependent SAXS of samples prepared from the dC16-1CW-P2K conjugate 16 in 25 mM phosphate buffer (16 wt %, first from top; 8 wt %, second; 4 wt %, third; 0.5 wt %, bottom). FIG. 20B shows the temperature dependent SAXS of samples prepared from the dC16-1CW-P2K conjugate 16 in 25 mM phosphate buffer upon heating from 25° C. to 85° C., at a ramp rate of 1° C./min and an equilibration time of 1 min prior to measurement. FIG. 20C shows the FRET spectra of a mixture of micelles prepared from the dC16-1CW-P2K conjugate 16 encapsulating DIL and DIO FRET pair dyes. The results demonstrate that minimal fluorescence due to energy transfer after 44 hours, indicating the absence of cargo leakage.

FIG. 21A shows distinct melting temperature of lipids in micelles composed of subunits with different headgroups. From top to bottom: SR-dC16-PEG2K conjugate 14, 1coi-W-KK-dC16 conjugate 19, 1CW-dC16-PEG2K conjugate 16 and 1CW-dC16-PEG5K conjugate 20. FIG. 21B shows DSC thermograms of 1CW-dC16-PEG2K with different treatments. From top to bottom: freshly made, 16 hr incubation at 20° C., 1 week incubation at 20° C., and annealed at 70° C. and slowly cooled to 20° C. The schematic drawings on the right display the evolution process of the headgroup arrangements.

FIG. 30A shows the UV-vis spectra of heme titrations into a ~4.3 µM solution of BB-dC16-P2K conjugate 8, a coiled-coil 4-helix bundle with four heme binding sites in the interior of the bundle. FIG. 30B shows the absorbance at 412 nm vs. the [heme]/[4-helix bundle] ratio for BB-dC16-P2K conjugate 8.

DETAILED DESCRIPTION OF THE INVENTION

I. General

The present invention provides conjugates of a peptide, polymer and lipid moiety, where the conjugates self-assemble to form trimers or tetramers, helix bundles, that then self-assemble to form nanoparticles. The nanoparticles can be loaded with a therapeutic or diagnostic agent for detection and/or treatment of a disease or condition. The conjugates can also be modified with another amino acid residue for binding to other biological moieties or other particles.

Figure 1:
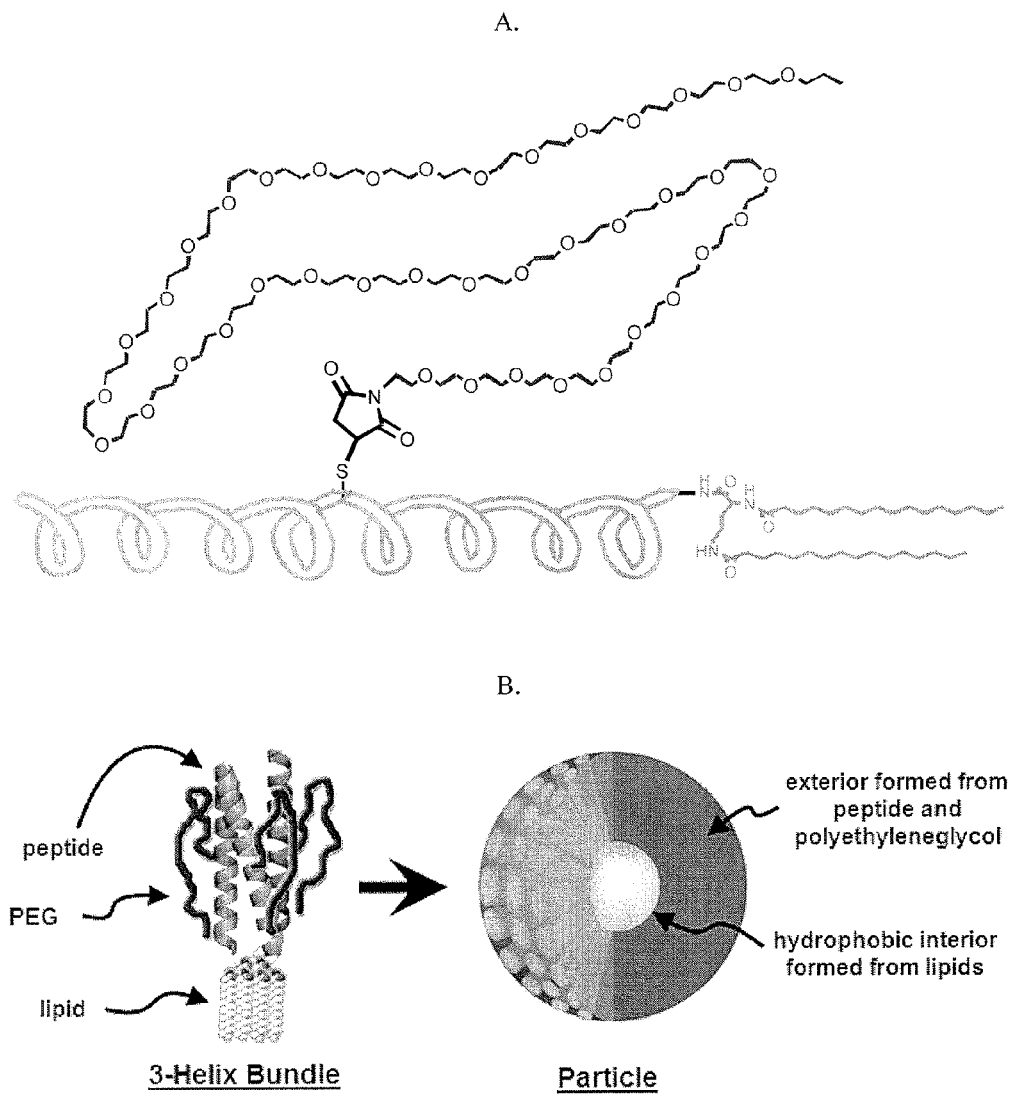
FIG. 1A shows a schematic of a lipid-peptide-polymer conjugate of the present invention using polyethyleneglycol (PEG) as the polymer.
FIG. 1B shows a schematic drawing of the lipidated 3-helix bundle-forming peptide-polymer conjugate and its assembly into higher order nanostructures.
Figure 2:
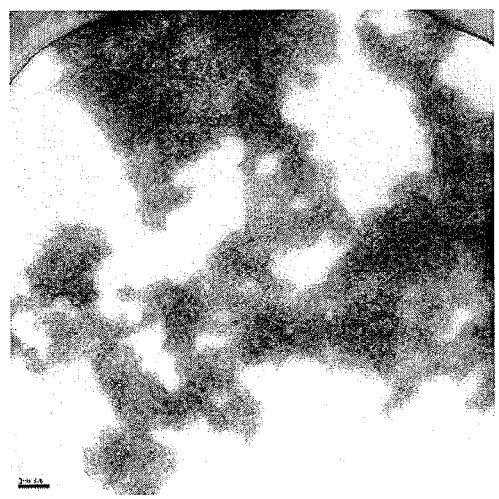
FIG. 2A shows a Transmission Electron Micrograph (TEM) of the particles prepared from the dC16-1coi-W-HHH conjugate 2.
FIG. 2B shows the MALDI-TOF of the dC16-1coi-W-HHH conjugate 2.
Figure 2:
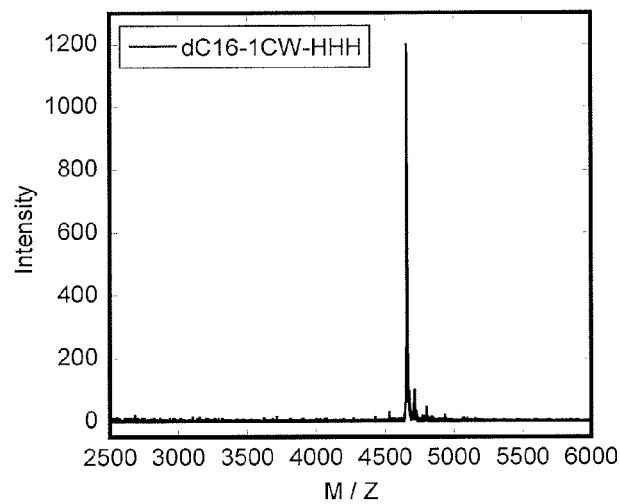
Figure 3:
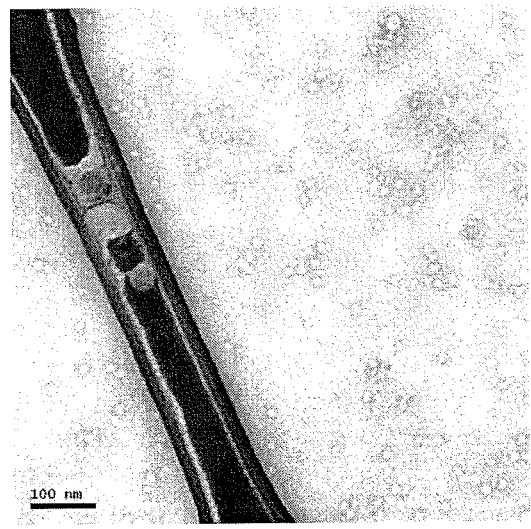
FIG. 3A shows a TEM image of the particles prepared from the dC16-1CW-P2K-EE conjugate 10.
FIG. 3B shows the MALDI-TOF of the dC16-1CW-P2K-EE conjugate 10.
Figure 3:
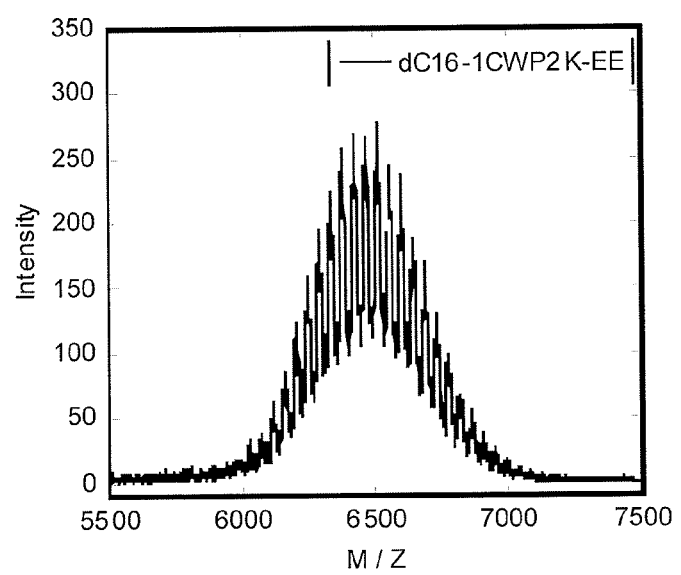
Figure 4:
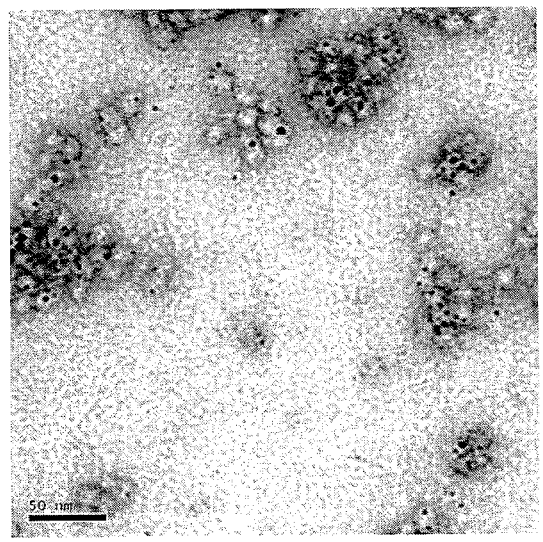
FIG. 4A shows a TEM image of the particles prepared from the dC16-1CW-P2K-GB conjugate 12 with gold particles and $NaBH_4$.
FIG. 4B shows the MALDI-TOF of the dC16-1CW-P2K-GB conjugate 12.
FIG. 4C shows a TEM image of the particles prepared from the dC16-1CW-P2K-GB conjugate 12 with gold particles only.
Figure 4:
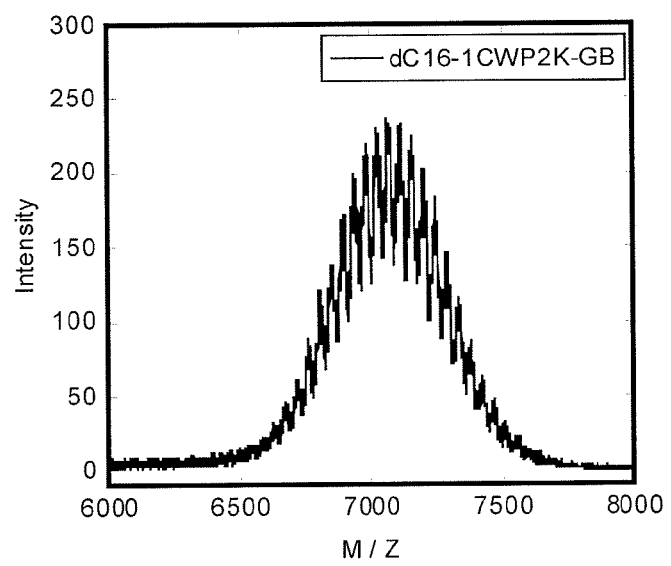
Figure 4:
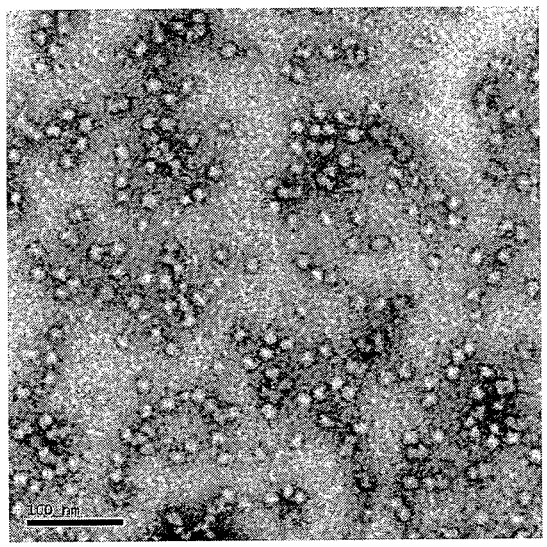
Figure 5:
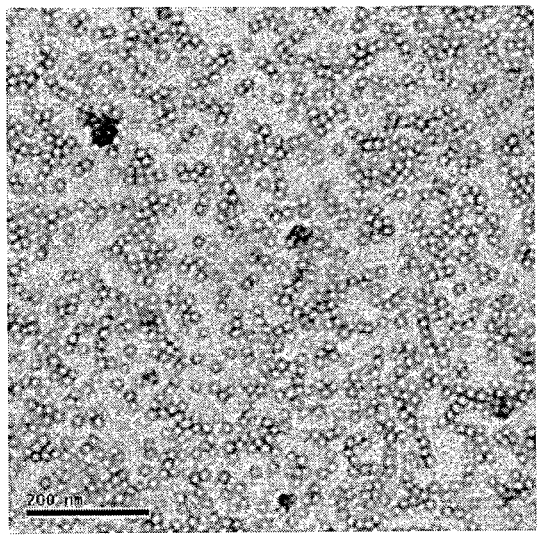
FIG. 5A shows a TEM image of the particles prepared from the dC16-1CW-P2K-HHH conjugate 1.
FIG. 5B shows the small-angle X-ray scattering (SAXS) of the particles prepared from the dC16-1CW-P2K-HHH conjugate 1 at both 4 wt. % (lower line) and 16 wt. % (upper line)
FIG. 5C shows the MALDI-TOF of the dC16-1CW-P2K-HHH conjugate 1.
Figure 5:
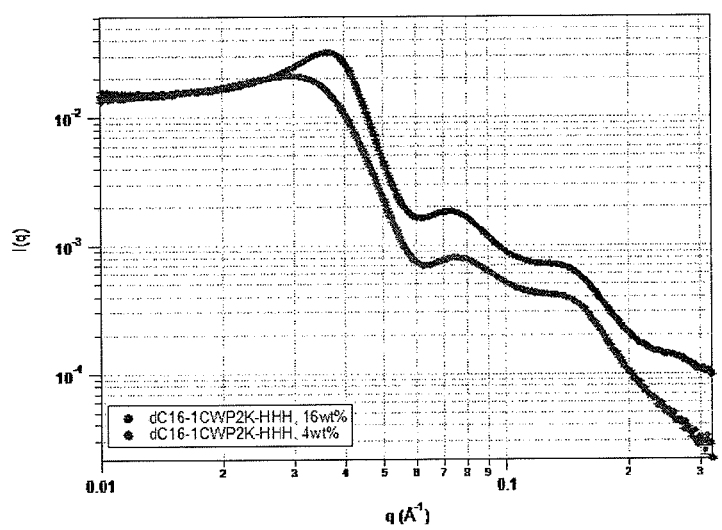
Figure 5:
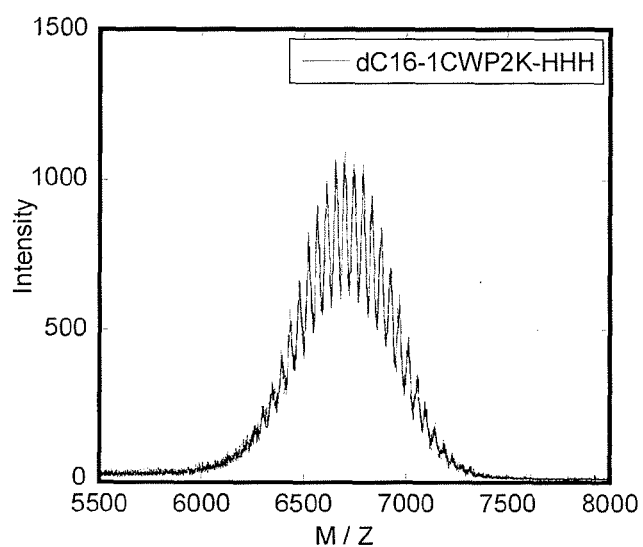
Figure 6:
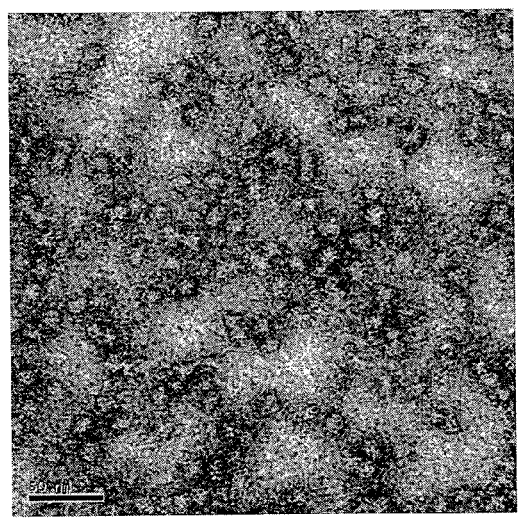
FIG. 6A shows a TEM image of the particles prepared from the dC16-1CW-P2K-KK conjugate 5.
FIG. 6B shows the small-angle X-ray scattering (SAXS) of the particles prepared from the dC16-1CW-P2K-KK conjugate 5 at both 4 wt. % (lower on the right) and 16 wt. % (upper on the right)
FIG. 6C shows the MALDI-TOF of the dC16-1CW-P2K-KK conjugate 5.
Figure 6:
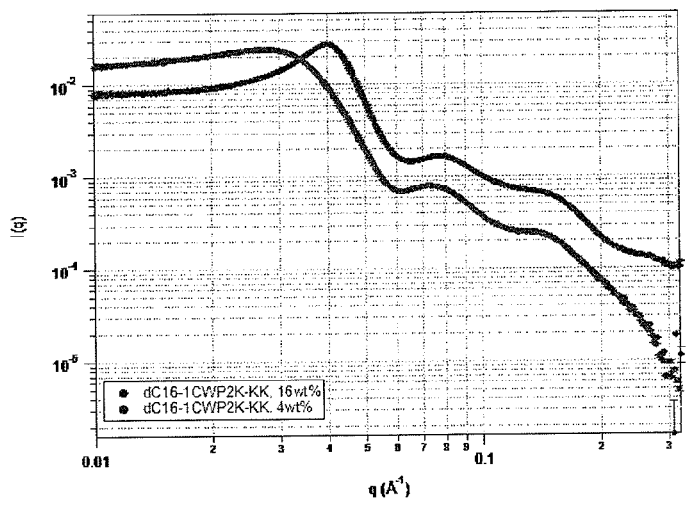
Figure 6:
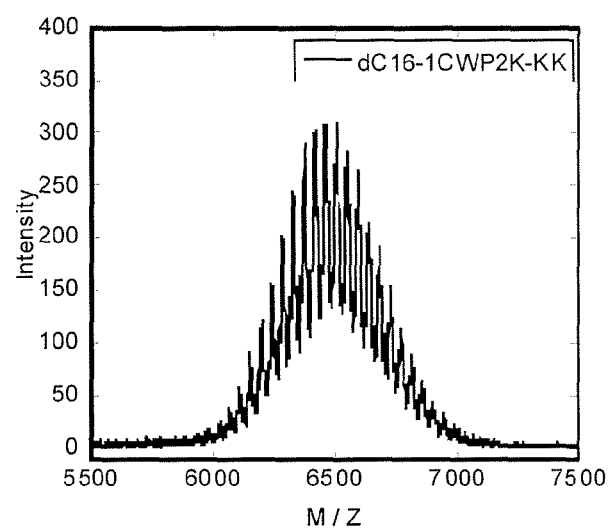
Figure 7:
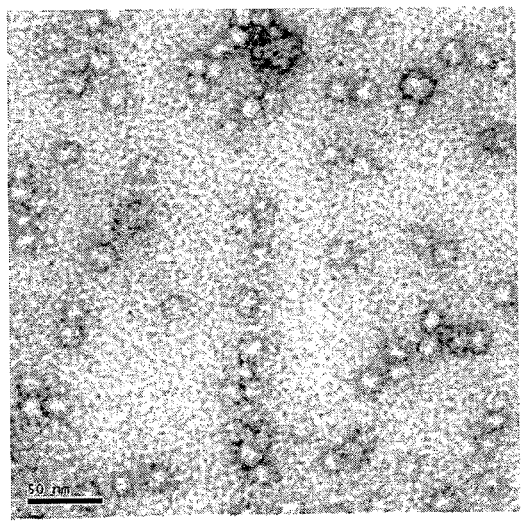
FIG. 7A shows a TEM image of the particles prepared from the dC16-1CW-P2K-RGD conjugate 11.
FIG. 7B shows the small-angle X-ray scattering (SAXS) of the particles prepared from the dC16-1CW-P2K-RGD conjugate 11 at 4 wt. %.
FIG. 7C shows the MALDI-TOF of the dC16-1CW-P2K-RGD conjugate 11.
Figure 7:
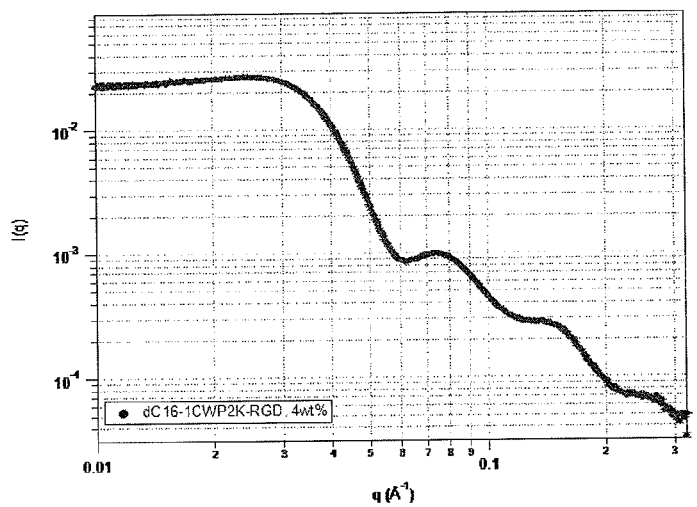
Figure 7:
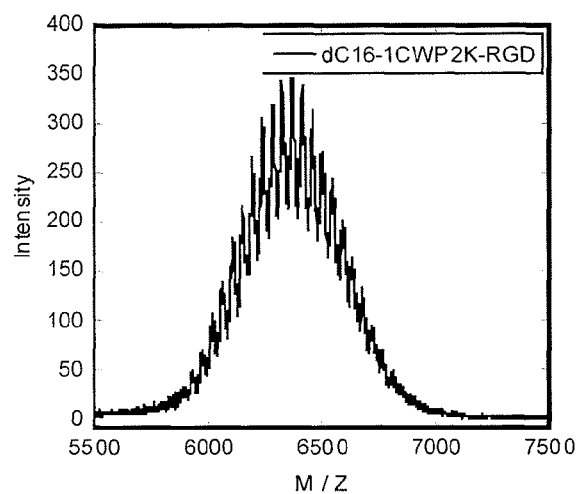
Figure 8:
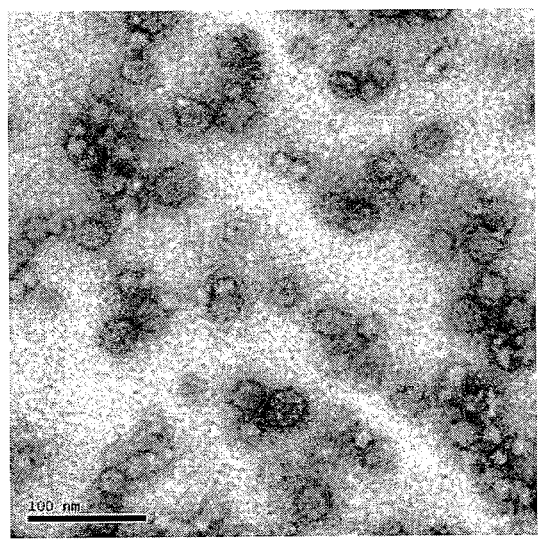
FIG. 8A shows a TEM image of the particles prepared from the dC16-1CW-P5K-HHH conjugate 3.
FIG. 8B shows the small-angle X-ray scattering (SAXS) of the particles prepared from the dC16-1CW-P5K-HHH conjugate 3 at both 4 wt. % (upper on the right) and 8 wt. % (lower on the right)
FIG. 8C shows the MALDI-TOF of the dC16-1CW-P5K-HHH conjugate 3.
Figure 8:
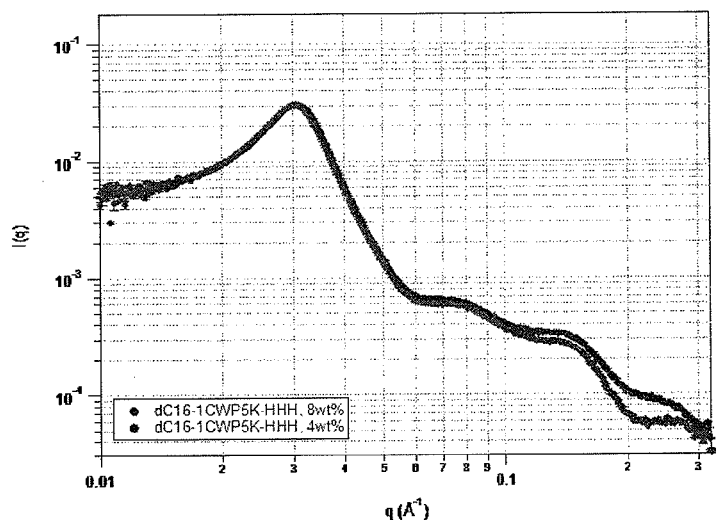
Figure 8:
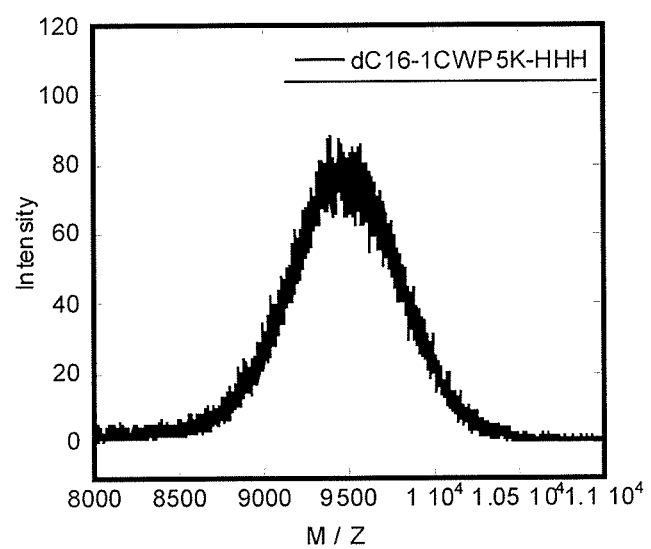
Figure 9:
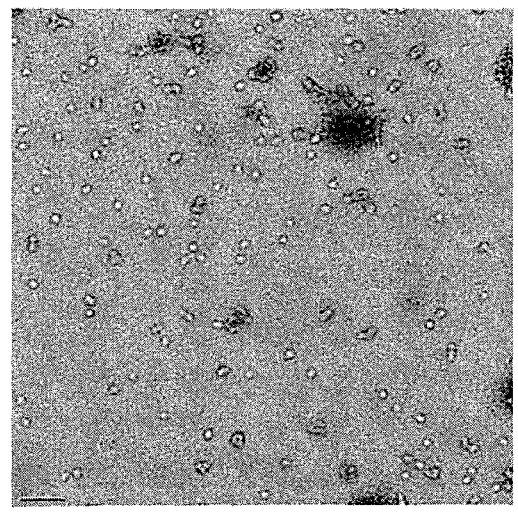
FIG. 9A shows a TEM image of the particles prepared from the dC16-BB-P2K conjugate 8.
FIG. 9B shows the MALDI-TOF of the dC16-BB-P2K conjugate 8.
Figure 9:
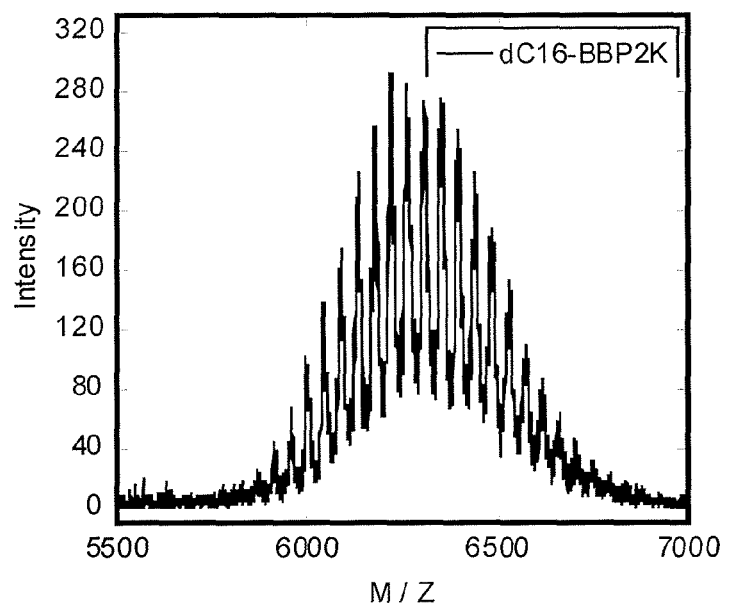
Figure 10:
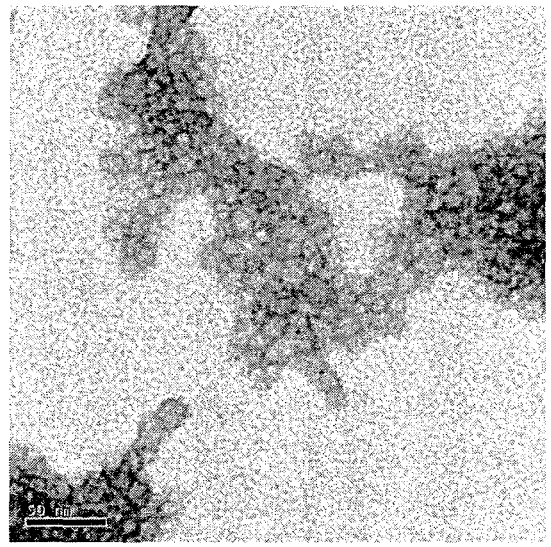
FIG. 10A shows a TEM image of the particles prepared from the PBD-1CW (end functionalization) conjugate 7.
FIG. 10B shows the MALDI-TOF of the PBD-1CW conjugate 7.
Figure 10:
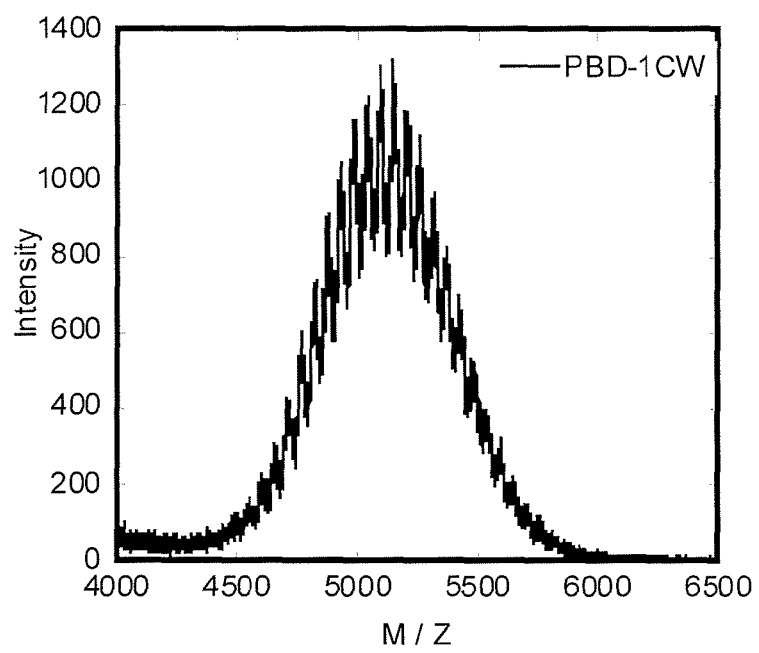

A schematic drawing of the conjugate and its formation into a higher order structure is depicted in FIG. 1. The conjugate is composed of coiled-coil 3-helix bundle-forming peptides, with hydrophobic di-alkyl tails conjugated to the N-terminus, and hydrophilic PEG coupled to the side of the peptide, forming an amphiphilic molecular building block with a cone-shaped geometry. Upon dissolution of the conjugates in aqueous buffer, phase separation occurs, leading to the formation of monodisperse nanoparticle with diameters in the range of 10-20 nm. The coiled-coils provide the chemical specificity and functionality unavailable with liposomes and polymersomes, and have the potential to order chemical cues laterally on the surface of the particle for site-specific targeting. The peptide helix acts as a rigid rod and determines the radial position of the polymer chains in a micelle. When micelles form, the polymer chains are confined and forced into close proximity and act like springs, affording a negative lateral pressure that imparts enhanced stability to the discrete micelles, much as repulsions can stabilize bulk assemblies of colloidal particles. Chemical specificity, size, and shape can also be tailored based on demand. Hydrophobic drugs can be encapsulated into the lipid core of the nanoparticle, or drugs can be linked to the peptide itself for high payloads. In a similar manner, imaging agents and genetic material can be incorporated. Specific immune responses can be elicited by presenting specific chemical cues on the surface at a high areal density.

II. Definitions

"Conjugate" refers to a compound having a polymer, peptide and lipid moiety all linked together. The conjugates are capable of self-assembling to form helix bundles. The helix bundles are prepared from 2 to 6 conjugates, typically 3 or 4.

"Polypeptide," "peptide," and "protein" are used interchangeably herein to refer to a polymer of amino acid residues. All three terms apply to amino acid polymers in which one or more amino acid residue is an artificial chemical mimetic of a corresponding naturally occurring amino acid, as well as to naturally occurring amino acid polymers and non-naturally occurring amino acid polymers. As used herein, the terms encompass amino acid chains of any length, including full-length proteins, wherein the amino acid residues are linked by covalent peptide bonds. The peptides of the present invention are helical in structure and form coiled-coil tertiary protein structure. The formation of coiled-coil tertiary structure provides a structural scaffold to position conjugated polymers and restrict the shape of individual sub-units for the nanoparticle. The helices also enhances the rigidity of the sub-unit and enable the geometric packing in a manner similar to that of virus particles.

"Polymer" refers to a macromolecule having repeating units connected by covalent bonds. Polymers can be hydrophilic, hydrophobic or amphiphilic. Hydrophilic polymers are substantially miscible with water and include, but are not limited to, polyethyleneglycol. Hydrophobic polymers are substantially immiscible with water and include, but are not limited to, polybutadiene and polystyrene. Amphiphilic polymers have both hydrophilic and hydrophobic properties and are typically block copolymers of a hydrophilic and a hydrophobic polymer. Polymers include homopolymers, random copolymers, block copolymers, and others. Specific polymers useful in the present invention include polyethyleneglycol, N-isopropylacrylamide (NIPAM), polybutadiene and polystyrene, among others.

"Hydrophobic moiety" refers to polymers or small molecules that are hydrophobic. Examples of hydrophobic moieties include, but are not limited to, hydrophobic polymers such as polybutadiene and polystyrene, as well as the lipid moieties of the present invention.

"Lipid moiety" refers to a moiety having at least one lipid. Lipids are small molecules having hydrophobic or amphiphilic properties and are useful for preparation of vesicles, micelles and liposomes. Lipids include, but are not limited to, fats, waxes, fatty acids, cholesterol, phospholipids, monoglycerides, diglycerides and triglycerides. The fatty acids can be saturated, mono-unsaturated or poly-unsaturated. Examples of fatty acids include, but are not limited to, butyric acid (C4), caproic acid (C6), caprylic acid (C8), capric acid (C10), lauric acid (C12), myristic acid (C14), palmitic acid (C16), palmitoleic acid (C16), stearic acid (C18), isostearic acid (C18), oleic acid (C18), vaccenic acid (C18), linoleic acid (C18), alpha-linoleic acid (C18), gamma-linolenic acid (C18), arachidic acid (C20), gadoleic acid (C20), arachidonic acid (C20), eicosapentaenoic acid (C20), behenic acid (C22), erucic acid (C22), docosahexaenoic acid (C22), lignoceric acid (C24) and hexacosanoic acid (C26). The lipid moiety can include several fatty acid groups using branching groups such as lysine and other branched amines.

"Anthracycline" refers to natural products of *Streptomyces peucetius* and related derivatives. Anthracyclines are glycosides containing an amino sugar and a fused, tetracyclic aglycone. Many anthracyclines demonstrate antibiotic and antineoplastic activity. Examples of anthracyclines include, but are not limited to, daunorubicin, doxorubicin, epirubicin, and idarubicin.

"Macrolide" refers to compounds characterized by a large (typically 14-to-16-membered) lactone ring substituted with pendant deoxy sugars. Many macrolides demonstrate antibiotic and immunomodulatory activity. Examples of macrolides include, but are not limited to, rapamycin, clarithromycin, and erythromycin.

"Therapeutic agent" refers to an agent capable of treating and/or ameliorating a condition or disease. Therapeutic agents include, but are not limited to, compounds, drugs, peptides, oligonucleotides, DNA, antibodies, and others.

"Diagnostic agent" refers to an agent capable of diagnosing a condition or disease. Diagnostic agents include, but are not limited to, dyes and radiolabels.

"Nucleic acid," "oligonucleotide," and "polynucleotide" refer to deoxyribonucleic acids (DNA) or ribonucleic acids (RNA) and polymers thereof in either single- or double-stranded form. Unless specifically limited, the term encompasses nucleic acids containing known analogues of natural nucleotides that have similar binding properties as the reference nucleic acid and are metabolized in a manner similar to naturally occurring nucleotides. The term nucleic acid is used interchangeably with gene, cDNA, and mRNA encoded by a gene.

"Contacting" refers to the process of bringing into contact at least two distinct species such that they can react. It should be appreciated, however, the resulting reaction product can be produced directly from a reaction between the added reagents or from an intermediate from one or more of the added reagents which can be produced in the reaction mixture.

The term "amino acid" refers to naturally occurring and synthetic amino acids, as well as amino acid analogs and amino acid mimetics that function in a manner similar to the naturally occurring amino acids. Naturally occurring amino acids are those encoded by the genetic code, as well as those amino acids that are later modified, e.g., hydroxyproline, γ-carboxyglutamate, and O-phosphoserine.

"Amino acid analogs" refers to compounds that have the same basic chemical structure as a naturally occurring amino acid, i.e., an a carbon that is bound to a hydrogen, a carboxyl group, an amino group, and an R group, e.g., homoserine, norleucine, methionine sulfoxide, methionine methyl sulfonium. Such analogs have modified R groups (e.g., norleucine) or modified peptide backbones, but retain the same basic chemical structure as a naturally occurring amino acid.

"Unnatural amino acids" are not encoded by the genetic code and can, but do not necessarily have the same basic structure as a naturally occurring amino acid. Unnatural amino acids include, but are not limited to azetidinecarboxylic acid, 2-aminoadipic acid, 3-aminoadipic acid, beta-alanine, aminopropionic acid, 2-aminobutyric acid, 4-aminobutyric acid, 6-aminocaproic acid, 2-aminoheptanoic acid, 2-aminoisobutyric acid, 3-aminoisobutyric acid, 2-aminopimelic acid, tertiary-butylglycine, 2,4-diaminoisobutyric acid, desmosine, 2,2'-diaminopimelic acid, 2,3-diaminopropionic acid, N-ethylglycine, N-ethylasparagine, homoproline, hydroxylysine, allo-hydroxylysine, 3-hydroxyproline, 4-hydroxyproline, isodesmosine, allo-isoleucine, N-methylalanine, N-methylglycine, N-methylisoleucine, N-methylpentylglycine, N-methylvaline, naphthalanine, norvaline, ornithine, pentylglycine, pipecolic acid and thioproline.

"Amino acid mimetics" refers to chemical compounds that have a structure that is different from the general chemical structure of an amino acid, but that functions in a manner similar to a naturally occurring amino acid.

Amino acids may be referred to herein by either the commonly known three letter symbols or by the one-letter symbols recommended by the IUPAC-IUB Biochemical Nomenclature Commission. Nucleotides, likewise, may be referred to by their commonly accepted single-letter codes.

"Conservatively modified variants" applies to both amino acid and nucleic acid sequences. With respect to particular nucleic acid sequences, "conservatively modified variants" refers to those nucleic acids that encode identical or essentially identical amino acid sequences, or where the nucleic acid does not encode an amino acid sequence, to essentially identical sequences. Because of the degeneracy of the genetic code, a large number of functionally identical nucleic acids encode any given protein. For instance, the codons GCA, GCC, GCG and GCU all encode the amino acid alanine. Thus, at every position where an alanine is specified by a codon, the codon can be altered to any of the corresponding codons described without altering the encoded polypeptide. Such nucleic acid variations are "silent variations," which are one species of conservatively modified variations. Every nucleic acid sequence herein that encodes a polypeptide also describes every possible silent variation of the nucleic acid. One of skill will recognize that each codon in a nucleic acid (except AUG, which is ordinarily the only codon for methionine, and TGG, which is ordinarily the only codon for tryptophan) can be modified to yield a functionally identical molecule. Accordingly, each silent variation of a nucleic acid that encodes a polypeptide is implicit in each described sequence.

As to amino acid sequences, one of skill will recognize that individual substitutions, deletions or additions to a nucleic acid, peptide, polypeptide, or protein sequence which alters, adds or deletes a single amino acid or a small percentage of amino acids in the encoded sequence is a "conservatively modified variant" where the alteration results in the substitution of an amino acid with a chemically similar amino acid (i.e., hydrophobic, hydrophilic, positively charged, neutral, negatively charged). Exemplified hydrophobic amino acids include valine, leucine, isoleucine, methionine, phenylalanine, and tryptophan. Exemplified aromatic amino acids include phenylalanine, tyrosine and tryptophan. Exemplified aliphatic amino acids include serine and threonine. Exemplified basic amino acids include lysine, arginine and histidine. Exemplified amino acids with carboxylate side-chains include aspartate and glutamate. Exemplified amino acids with carboxamide side chains include asparagines and glutamine. Conservative substitution tables providing functionally similar amino acids are well known in the art. Such conservatively modified variants are in addition to and do not exclude polymorphic variants, interspecies homologs, and alleles of the invention.

The following eight groups each contain amino acids that are conservative substitutions for one another:
1) Alanine (A), Glycine (G);
2) Aspartic acid (D), Glutamic acid (E);
3) Asparagine (N), Glutamine (Q);
4) Arginine (R), Lysine (K);
5) Isoleucine (I), Leucine (L), Methionine (M), Valine (V);
6) Phenylalanine (F), Tyrosine (Y), Tryptophan (W);
7) Serine (S), Threonine (T); and
8) Cysteine (C), Methionine (M)
(see, e.g., Creighton, Proteins (1984)).

"Helix bundle" refers to a structure formed by the self-assembly of a plurality of conjugates of the present invention, where the hydrophobic moieties and peptides of each conjugate are aligned with each other.

III. Conjugates, Helix Bundles and Particles

The present invention provides conjugates of a peptide, polymer and lipid moiety, where the conjugates self-assemble to form trimers or tetramers of helix bundles, that then self-assemble to form nanoparticles.

In some embodiments, the present invention provides a conjugate having a peptide with from about 10 to about 100 amino acids, wherein the peptide adopts a helical structure. The conjugate also includes a first polymer covalently linked to the peptide, and a hydrophobic moiety covalently linked to the N-terminus of the peptide, wherein the hydrophobic moiety comprises a second polymer or a lipid moiety.

Peptides useful in the conjugates of the present invention are those that adopt a helical conformation. The peptides can be of any suitable length, such as from about 10 to about 1000 amino acids, or from about 10 to about 500 amino acids, or from about 10 to about 100 amino acids. In some embodiments, the peptide can be SEQ ID NO: 1 (1CW), SEQ ID NO: 2 (BB), SEQ ID NO: 4 (SR), and SEQ ID NO: 5 (1coi-W).

In a preferred embodiment, the present invention comprises peptide sequences that self-associate. In other embodiment, the peptide sequence can be a de novo designed 3-helix bundle peptide, such as, but not limited to SEQ ID NO: 1 (1CW). In particular aspects, additional 1-50 amino acids can be appended to the C-terminus of the peptide without interfering with micelle formation. In some embodiments, the peptide includes an additional 1-25 amino acids at the C-terminus, preferably 1-10, more preferably 1-5. In another embodiment, the peptide sequence can be a control peptide sequence that form random coil, such as, but not limited to SEQ ID NO: 4 (SR). The peptide can be designed based on SEQ ID NO:5 (1coi-W), and have similar characteristics including PI and hydrophobicity. In yet another embodiment, the peptide sequence can be a heme-binding peptide that is able to form 4-helix bundles such as SEQ ID NO: 2 (BB).

The conjugates of the present invention also include a first polymer. The first polymer can be any suitable polymer. Exemplary first polymers include hydrophilic, hydrophobic and amphiphilic polymers. Some polymers useful as the first polymer of the present invention include, but are not limited to, polyethyleneglycol (PEG or P), poly(N-isopropylacrylamide) (NIPAM), polybutadiene (PBD) and polystyrene (PS). In some embodiments, the first polymer is a hydrophilic polymer. Hydrophilic polymers are miscible with water, and include, but are not limited to, polyethyleneglycol, NIPAM, and cellulose. In some other embodiments, the first polymer is polyethyleneglycol.

The first polymer can be linked to any point of the peptide, such as the N-terminus, the C-terminus and at any amino acid along the peptide chain. The first polymer can be linked to the peptide via covalent, ionic and other attachment means. In some embodiments, the first polymer is linked to the peptide via covalent bonds. In other embodiments, the first polymer is linked to the peptide at an amino acid other than the N- or C-terminus. Any suitable covalent linkage is useful for attaching the first polymer to the peptide. For example, the covalent linkage can be via an ester, amide, ether, thioether or carbon linkage. In some embodiments, the first polymer can be modified with a maleimide that reacts with a sulfhydryl group of the peptide, such as on a cysteine. In other embodiments, the first polymer is linked to the peptide via click chemistry, by reaction of an azide and an alkyne to form a triazole ring.

In some embodiments, the hydrophobic moiety can be a second polymer. Polymers useful as the hydrophobic moiety include hydrophobic polymers which include, but are not limited to, polybutadiene, polystyrene, polyacrylates, polymethacrylates, polydiacetylene and others. In some other embodiments, the hydrophobic moiety can be polybutadiene.

In other embodiments, the hydrophobic moiety can be a lipid moiety. Lipid moieties useful in the present invention include from 1 to 20 long alkyl chains, from 1 to 10 alkyl chains, or from 1 to 6 alkyl chains, or 1, 2, 3, 4, 5, 6, 7, 8, 9 or 10 alkyl chains. The lipid moieties can be prepared from fatty acids, which include, but are not limited to, capric acid (C10), lauric acid (C12), myristic acid (C14), palmitic acid (C16), palmitoleic acid (C16), stearic acid (C18), isostearic acid (C18), oleic acid (C18), vaccenic acid (C18), linoleic acid (C18), alpha-linoleic acid (C18), gamma-linolenic acid (C18), arachidic acid (C20), gadoleic acid (C20), arachidonic acid (C20), eicosapentaenoic acid (C20), behenic acid (C22), erucic acid (C22), docosahexaenoic acid (C22), lignoceric acid (C24) and hexacosanoic acid (C26).

Exemplary alkyl groups in the lipid moieties include $C_{10-20}$ alkyl chains, such as $C_{10}$, $C_{12}$, $C_{14}$, $C_{16}$, $C_{18}$, or $C_{20}$ alkyl groups. The alkyl groups can be saturated or partially unsaturated. In some embodiments, the lipid moieties have at least one $C_{14}$ alkyl group, or at least one $C_{16}$ alkyl group. When the lipid moieties include more than one alkyl group, the lipid moiety also includes a branched linker providing for attachment of multiple alkyl groups. The branched linkers useful in the present invention include, but are not limited to, lysine, glutamic acid and other branched amines and carboxylic acids. In some embodiments, the lipid moiety includes from 1 to 6 $C_{10-20}$ alkyl groups. The lipid moiety can include 1, 2, 3, 4, 5 or 6 $C_{10-20}$ alkyl groups. In other embodiments, the lipid moiety includes 1, 2, or 4 $C_{10-20}$ alkyl groups. In still other embodiments, the lipid moiety includes 1 $C_{10-20}$ alkyl group. In yet other embodiments, the lipid moiety includes 2 $C_{10-20}$ alkyl groups.

The hydrophobic moiety can be attached to the peptide at any useful point on the peptide, such as at the N-terminus, C-terminus, or anywhere along the length of the peptide. In some embodiments, the hydrophobic moiety is linked to the peptide at the N-terminus.

When the first polymer is linked to the peptide at a point other than the N- or C-terminus, and the hydrophobic moiety is linked to the N-terminus, the conjugates of the present invention can also include a component linked to the C-terminus. The component at the C-terminus can be any useful binding or labeling moiety which can include, but is not limited to, an amino acid residue, a oligonucleotide, a polypeptide, an antibody, a diagnostic agent, a therapeutic agent, a polymer, and others. In some embodiments, the conjugate includes an amino acid residue linked to the C-terminus of the peptide. The amino acid residue can have any suitable number of amino acids, such as from 2 to about 100, or from 2 to about 50, or from 2 to about 20 amino acids. In other embodiments, the amino acid residue can be GGG, HHH, KK, EE, RGD and AYSSGAPPMPPF, and combinations thereof. Other amino acid residues are useful in the conjugates of the present invention.

In another embodiment, the conjugate includes the peptide of SEQ ID NO: 1 (1CW), polyethyleneglycol as the first polymer, the hydrophobic moiety having lysine and two $C_{16}$ alkyl chains, and an amino acid residue of from 2 to about 20 amino acids covalently linked to the C-terminus of the peptide. In some other embodiments, the conjugate includes the peptide of SEQ ID NO: 1 (1CW), polyethyleneglycol as the first polymer, the hydrophobic moiety having lysine and two $C_{18}$ alkyl chains, and an amino acid residue of from 2 to about 20 amino acids covalently linked to the C-terminus of the peptide.

In another embodiment, the amphiphile is constructed by covalently linking polyethylene glycol (PEG) of 2000 Da (PEG2k or P2K) to the Cys14 of a 3-helix bundle-forming peptide of SEQ ID NO:1 (1CW). Two C16 alkyl chains are attached to the peptide N-terminus with a (6)-amino-hexanoic acid linker inserted between the peptide and the double C16 tail. In another embodiment the peptide amphiphile of SEQ ID NO: 5 (1coi-W) can be unconjugated to any polymer.

The present invention also provides helix bundles, formed from the self-assembly of a plurality of conjugates. The helix bundles can be formed from 2, 3, 4, 5, 6, 7, 8, 9 or 10 conjugates. In some embodiments, the present invention provides a helix bundle having from 2 to 6 conjugates of the present invention. In other embodiments, the helix bundles includes 3 conjugates. In some other embodiments, the helix bundle includes 4 conjugates.

The present invention also provides particles formed from the self-assembly of the helix bundles, such that the hydrophobic moiety forms a micellar structure having a hydrophobic pocket, and the peptide and first polymer are on the exterior of the micelle formed by the hydrophobic moiety. The particles include any suitable number of conjugates. In some embodiments, the present invention provides a particle having from about 20 to about 200 conjugates of the present invention. The particles can be of any suitable size. For example, the particles can be from about 5 nm to about 500 nm in diameter, or from about 5 to about 100 nm in diameter, or from about 5 nm to about 50 nm in diameter, or from about 5 nm to about 25 nm in diameter.

The particles of the present invention can include cargo in the hydrophobic interior of the particle. Cargo useful in the particles of the present invention include, but are not limited to, a therapeutic agent, a diagnostic agent, DNA and an oligonucleotide. Examples of therapeutic agents include, but are not limited to, anthracyclines (such as doxorubicin, daunorubicin, epirubicin, and the like), macrolides (such as rapamycin, fujimycin, pimecrolimus, and the like), alkylating agents (such as temozolomide, procarbazine, altretamine, and the like), taxanes, and vinca alkaloids. Examples of diagnostic agents include, but are not limited to, chromophores, fluorophores, and radionuclides. The conjugates, helix bundles and particles of the present invention can be linked to other particles, such as gold nanoparticles and magnetic nanoparticles that are typically a few nanometers in diameter for imaging and manipulation purposes. In some embodiments, the invention provides particles as described above, wherein each additional agent is independently selected from a fluorophore, a radionuclide, an anthracycline, and a macrolide. In some embodiments, each additional agent is independently selected from doxorubicin and rapamycin. Alternatively, the additional agents be covalently or noncovalently bound to one of, a combination of, or all of the peptide component, the first polymeric component, and the second polymeric component of the amphiphilic conjugates.

The conjugates, helix bundles and particles of the present invention can be linked to other particles, such as gold nanoparticles and magnetic nanoparticles that are typically a few nanometers in diameter for imaging and manipulation purposes.

TABLE 1

Conjugates

| Conjugate | N-terminus[1] | Peptide[2] | First Polymer[3] | C-terminus Amino Acid Residue | Particle Size (nm) |
|---|---|---|---|---|---|
| 1 | dC16 | 1CW | PEG2K | HHH | 16 nm |
| 2 | dC16 | 1coi-W | — | HHH | 8-10 nm |
| 3 | dC16 | 1CW | PEG5K | HHH | 20-50 nm |
| 4 | sC16 | 1CW | PEG2K | KK | 10-13 nm |
| 5 | dC16 | 1CW | PEG2K | KK | 14-17 nm |
| 6 | tC16 | 1CW | PEG2K | KK | nanorods 10 nm in diameter |
| 7 | PBD | 1CW | — | — | 10-13 nm |
| 8 | dC16 | BB | PEG2K | — | 10-15 nm |
| 9 | MeC(O) | BB | PS | — | 10-12 nm |
| 10 | dC16 | 1CW | PEG2K | EE | 14-17 nm |
| 11 | dC16 | 1CW | PEG2K | RGD | 14-17 nm |
| 12 | dC16 | 1CW | PEG2K | GB[4] | 14-17 nm |
| 13 | sC14 | 1CW | PEG2K | DGR | 10-13 nm |
| 14 | dC16 | SR | PEG2K | — | 10-15 nm |
| 15 | dC18 | 1CW | PEG2K | — | 12-15 nm |
| 16 | dC16 | 1CW | PEG2K | — | 10-15 nm |
| 17 | dC16 | 1CW | PEG2K | KK($K_{FI}$)[5] | — |
| 18 | dC16 | SR | PEG2K | KK($K_{FI}$)[5] | — |
| 19 | dC16 | 1coi-W | PEG2K | KK | — |
| 20 | dC16 | 1CW | PEG5K | — | — |

[1]The "s", "d" and "t" refers to the number of fatty acid chains in the lipid moiety: 1, 2, and 4, respectively. The "C16" refers to the number of carbons in the fatty acid chain, such as myristic acid (C14) palmitic acid (C16) and stearic acid (C18). PBD is polybutadiene.
[2]1CW is SEQ ID NO: 1; BB is SEQ ID NO: 2; SR is SEQ ID NO: 4; 1coi-W is SEQ ID NO: 5. Conjugates 1-6, 10-12, and 17-18 contain a GGG linker sequence between the peptide and the C-terminus amino acid residue.
[3]PEG is polyethyleneglycol; PS is polystyrene. Polymer attached at Cys-14.
[4]GB is AYSSGAPPMPPF, SEQ ID NO: 3.
[5]$K_{FI}$ is lysine with carboxyfluorescein conjugated to the side chain ε-amino group. As used throughout the instant application, the conjugates of the present invention can be written in shorthand as dC16-1CW-PEG2K or 1CW-dC16-PEG2K or any other combination of the three components.

IV. Methods of Preparing Nanoparticles

The nanoparticles of the present invention can be prepared by any suitable method known to one of skill in the art. For example, the nanoparticles can be prepared by first dissolving the conjugates in a suitable solvent at any concentration from about 1 nM to about 1M, or from about 1 μM to about 100 mM, or from about 1 mM to about 100 mM. Alternatively, the conjugates can be dissolved to form from about 0.1 to about 50 wt. % of the solution, or from about 1 to about 50 wt. %, or from about 1 to about 25 wt. %. The conjugates self-assemble to form the helix bundles of the present invention. The helix bundles then self-assemble to form the particles. In some embodiments, the present invention provides a method of forming particles of the present invention by contacting a plurality of conjugates of the present invention such that the conjugates self-assemble to form the particles of the present invention.

In an aqueous solvent, the conjugates of the present invention can self-assemble such that the hydrophilic portion is oriented towards the exterior of the nanocarrier and the hydrophobic portion is oriented towards the interior, thus forming a micelle. When a non-polar solvent is used, an inverse micelle can be formed where the hydrophilic portion is oriented towards the interior of the nanocarrier and the hydrophobic portion is oriented towards the exterior of the nanocarrier.

The present invention also provides for particles prepared by dissolving the conjugates of the present invention at a concentration as described above, such that the conjugates self-assemble to form helix bundles, and then allowing the helix bundles to self-assemble to form the particles of the present invention.

V. Methods for Drug Delivery

In some embodiments, the present invention provides a method for delivering a diagnostic or therapeutic agent to a subject comprising administering a particle to the subject. In some embodiments, the particle encapsulates the diagnostic or therapeutic agent. In other embodiments, the diagnostic or therapeutic agent is conjugated or coupled to the particle of the present invention. Thus, the particle includes from about 20 to about 200 conjugates of the present invention and the diagnostic or therapeutic agent to be delivered. In some embodiments, the therapeutic agent is selected from the group consisting of doxorubicin, temzolomide, and rapamycin.

Delivery of the therapeutic agent can be conducted such that drug-loaded micelles selectively accumulate at a desired site in a subject, such as a specific organ or a tumor. In some cases, micelle accumulation at a target site may be due to the enhanced permeability and retention characteristics of certain tissues such as cancer tissues. Accumulation in such a manner can arise, in part, from the micelle size and may not require special targeting functionality. In other cases, the micelles of the present invention can also include ligands for active targeting as described above. Target delivery can also be accomplished by administering drug-loaded micelles directed to a desired site. In some embodiments, delivery of a therapeutic agent can include administering a particle of the present invention via intratumoral infusion.

The nanoparticles of the present invention can be used to deliver any suitable cargo in a targeted or untargeted fashion. Suitable cargo includes, but is not limited to, vaccines, nucleic acids such as DNA or RNA, peptides, proteins, imaging agents, and drugs. The nanoparticles of the present invention are also useful for gene therapy, the administration of an expressed or expressible nucleic acid to a subject.

The nanocarrier cargo can be encapsulated within the nanocarrier

Targeting Agents

Generally, the targeting agents of the present invention can associate with any target of interest, such as a target associated with an organ, tissues, cell, extracellular matrix, or intracellular region. In certain embodiments, a target can be associated with a particular disease state, such as a cancerous condition. In some embodiments, the targeting component can be specific to only one target, such as a receptor. Suitable targets can include but are not limited to a nucleic acid, such as a DNA, RNA, or modified derivatives thereof. Suitable targets can also include but are not limited to a protein, such as an extracellular protein, a receptor, a cell surface receptor, a tumor-marker, a transmembrane protein, an enzyme, or an antibody. Suitable targets can include a carbohydrate, such as a monosaccharide, disaccharide, or polysaccharide that can be, for example, present on the surface of a cell.

In certain embodiments, a targeting agent can include a target ligand, a small molecule mimic of a target ligand, or an antibody or antibody fragment specific for a particular target. In some embodiments, a targeting agent can further include folic acid derivatives, B-12 derivatives, integrin RGD peptides, NGR derivatives, somatostatin derivatives or peptides that bind to the somatostatin receptor, e.g., octreotide and octreotate, and the like. The targeting agents of the present invention can also include an aptamer. Aptamers can be designed to associate with or bind to a target of interest. Aptamers can be comprised of, for example, DNA, RNA, and/or peptides, and certain aspects of aptamers are well known in the art. (See. e.g., Klussman, S., Ed., The Aptamer Handbook, Wiley-VCH (2006); Nissenbaum, E. T., *Trends in Biotech*. 26(8): 442-449 (2008)).

Therapeutic Agents

The therapeutic agent or agents used in the present invention can include any agent directed to treat a condition in a subject. In general, any therapeutic agent known in the art can be used, including without limitation agents listed in the United States Pharmacopeia (U.S.P.), *Goodman and Gilman's The Pharmacological Basis of Therapeutics*, 10$^{th}$ Ed., McGraw Hill, 2001; Katzung, Ed., *Basic and Clinical Pharmacology*, McGraw-Hill/Appleton & Lange, 8$^{th}$ ed., Sep. 21, 2000; *Physician's Desk Reference* (Thomson Publishing; and/or *The Merck Manual of Diagnosis and Therapy*, 18$^{th}$ ed., 2006, Beers and Berkow, Eds., Merck Publishing Group; or, in the case of animals, *The Merck Veterinary Manual*, 9$^{th}$ ed., Kahn Ed., *Merck Publishing Group*, 2005; all of which are incorporated herein by reference.

Therapeutic agents can be selected depending on the type of disease desired to be treated. For example, certain types of cancers or tumors, such as carcinoma, sarcoma, leukemia, lymphoma, myeloma, and central nervous system cancers as well as solid tumors and mixed tumors, can involve administration of the same or possibly different therapeutic agents. In certain embodiments, a therapeutic agent can be delivered to treat or affect a cancerous condition in a subject and can include chemotherapeutic agents, such as alkylating agents, antimetabolites, anthracyclines, alkaloids, topoisomerase inhibitors, and other anticancer agents. In some embodiments, the agents can include antisense agents, microRNA, siRNA and/or shRNA agents.

Therapeutic agents can include an anticancer agent or cytotoxic agent including but not limited to avastin, doxorubicin, temzolomide, rapamycin, platins such as cisplatin, oxaliplatin and carboplatin, cytidines, azacytidines, 5-fluorouracil (5-FU), gemcitabine, capecitabine, camptothecin, bleomycin, daunorubicin, vincristine, topotecan or taxanes, such as paclitaxel and docetaxel.

Therapeutic agents of the present invention can also include radionuclides for use in therapeutic applications. For example, emitters of Auger electrons, such as $^{111}$In, can be combined with a chelate, such as diethylenetriaminepentaacetic acid (DTPA) or 1,4,7,10-tetraazacyclododecane-1,4,7,10-tetraacetic acid (DOTA), and included in a nanoparticle to be used for treatment. Other suitable radionuclide and/or radionuclide-chelate combinations can include but are not limited to beta radionuclides ($^{177}$Lu, $^{153}$Sm, $^{88/90}$Y) with DOTA, $^{64}$Cu-TETA, $^{188/186}$Re(CO)$_3$-IDA; $^{188/186}$Re(CO) triamines (cyclic or linear), $^{188/186}$Re(CO)$_3$-Enpy2, and $^{188/186}$Re(CO)$_3$-DTPA.

Diagnostic Agents

A diagnostic agent used in the present invention can include any diagnostic agent known in the art, as provided, for example, in the following references: Armstrong et al., *Diagnostic Imaging*, 5$^{th}$ Ed., Blackwell Publishing (2004); Torchilin, V. P., Ed., *Targeted Delivery of Imaging Agents*, CRC Press (1995); Vallabhajosula, S., *Molecular Imaging: Radiopharmaceuticals for PET and SPECT*, Springer (2009). A diagnostic agent can be detected by a variety of ways, including as an agent providing and/or enhancing a detectable signal that includes, but is not limited to, gamma-emitting, radioactive, echogenic, optical, fluorescent, absorptive, magnetic or tomography signals. Techniques for imaging the diagnostic agent can include, but are not limited to, single photon emission computed tomography (SPECT), magnetic resonance imaging (MRI), optical imaging, positron emission tomography (PET), computed tomography (CT), x-ray imaging, gamma ray imaging, and the like.

In some embodiments, a diagnostic agent can include chelators that bind to metal ions to be used for a variety of diagnostic imaging techniques. Exemplary chelators include but are not limited to ethylenediaminetetraacetic acid (EDTA), [4-(1,4,8,11-tetraazacyclotetradec-1-yl)methyl] benzoic acid (CPTA), cyclohexanediaminetetraacetic acid (CDTA), ethylenebis(oxyethylenenitrilo)tetraacetic acid (EGTA), diethylenetriaminepentaacetic acid (DTPA), citric acid, hydroxyethyl ethylenediamine triacetic acid (HEDTA), iminodiacetic acid (IDA), triethylene tetraamine hexaacetic acid (TTHA), 1,4,7,10-tetraazacyclododecane-1,4,7,10-tetra (methylene phosphonic acid) (DOTP), 1,4,8,11-tetraazacyclododecane-1,4,8,11-tetraacetic acid (TETA), 1,4,7,10-tetraazacyclododecane-1,4,7,10-tetraacetic acid (DOTA), and derivatives thereof.

A radioisotope can be incorporated into some of the diagnostic agents described herein and can include radionuclides that emit gamma rays, positrons, beta and alpha particles, and X-rays. Suitable radionuclides include but are not limited to $^{225}$Ac, $^{72}$As, $^{211}$At, $^{11}$B, $^{128}$Ba, $^{212}$Bi, $^{75}$Br, $^{77}$Br, $^{14}$C, $^{109}$Cd, $^{62}$Cu, $^{64}$Cu, $^{67}$Cu, $^{18}$F, $^{67}$Ga, $^{68}$Ga, $^{3}$H, $^{123}$I, $^{125}$I, $^{130}$I, $^{131}$I, $^{111}$In, $^{177}$Lu, $^{13}$N, $^{15}$O, $^{32}$P, $^{33}$P, $^{212}$Pb, $^{103}$Pd, $^{186}$Re, $^{188}$Re, $^{47}$Sc, $^{153}$Sm, $^{89}$Sr, $^{99m}$Tc, $^{88}$Y and $^{90}$Y. In certain embodiments, radioactive agents can include $^{111}$In-DTPA, $^{99m}$Tc(CO)$_3$-DTPA, $^{99m}$Tc(CO)$_3$-ENPy2, $^{62/64/67}$Cu-TETA, $^{99m}$Tc(CO)$_3$-IDA, and $^{99m}$Tc(CO)$_3$triamines (cyclic or linear). In other embodiments, the agents can include DOTA and its various analogs with $^{111}$In, $^{177}$Lu, $^{153}$Sm, $^{88/90}$Y, $^{62/64/67}$Cu, or $^{67/68}$Ga. In some embodiments, the micelles can be radiolabeled, for example, by incorporation of chelating groups, such as DTPA-lipid, as provided in the following references: Phillips et al., *Wiley Interdisciplinary Reviews: Nanomedicine and Nanobiotechnology*, 1(1): 69-83 (2008); Torchilin, V. P. & Weissig, V., Eds. *Liposomes 2nd Ed.*: Oxford Univ. Press (2003); Elbayoumi, T. A. & Torchilin, V. P., *Eur. J. Nucl. Med. Mol. Imaging*. 33:1196-1205 (2006); Mougin-Degraef, M. et al., *Int'l J. Pharmaceutics* 344:110-117 (2007).

In other embodiments, the diagnostic agents can include optical agents such as fluorescent agents, phosphorescent agents, chemiluminescent agents, and the like. Numerous agents (e.g., dyes, probes, labels, or indicators) are known in the art and can be used in the present invention. (See, e.g., Invitrogen, The Handbook—A Guide to Fluorescent Probes and Labeling Technologies, Tenth Edition (2005)). Fluorescent agents can include a variety of organic and/or inorganic small molecules or a variety of fluorescent proteins and derivatives thereof. For example, fluorescent agents can include but are not limited to cyanines, phthalocyanines, porphyrins, indocyanines, rhodamines, phenoxazines, phenylxanthenes, phenothiazines, phenoselenazines, fluoresceins, benzoporphyrins, squaraines, dipyrrolo pyrimidones, tetracenes, quinolines, pyrazines, corrins, croconiums, acridones, phenanthridines, rhodamines, acridines, anthraquinones, chalcogenopyrylium analogues, chlorins, naphthalocyanines, methine dyes, indolenium dyes, azo compounds, azulenes, azaazulenes, triphenyl methane dyes, indoles, benzoindoles, indocarbocyanines, benzoindocarbocyanines, and BODIPY™ derivatives having the general structure of 4,4-difluoro-4-bora-3a,4a-diaza-s-indacene, and/or conjugates and/or derivatives of any of these. Other agents that can be used include, but are not limited to, for example, fluorescein, fluorescein-polyaspartic acid conjugates, fluorescein-polyglutamic acid conjugates, fluorescein-polyarginine conjugates, indocyanine green, indocyanine-dodecaaspartic acid conjugates, indocyanine-polyaspartic acid conjugates, isosulfan blue, indole disulfonates, benzoindole disulfonate, bis(ethylcarboxymethyl)indocyanine, bis(pentylcarboxymethyl)indocyanine, polyhydroxyindole sulfonates, polyhydroxybenzoindole sulfonate, rigid heteroatomic indole sulfonate, indocyaninebispropanoic acid, indocyaninebishexanoic acid, 3,6-dicyano-2,5-[(N,N,N',N'-tetrakis(carboxymethyl)amino]pyrazine, 3,6-[(N,N,N',N'-tetrakis(2-hydroxyethyl)amino]pyrazine-2,5-dicarboxylic acid, 3,6-bis(N-azatedino)pyrazine-2,5-dicarboxylic acid, 3,6-bis(N-morpholino)pyrazine-2,5-dicarboxylic acid, 3,6-bis(N-piperazino)pyrazine-2,5-dicarboxylic acid, 3,6-bis(N-thiomorpholino)pyrazine-2,5-dicarboxylic acid, 3,6-bis(N-thiomorpholino)pyrazine-2,5-dicarboxylic acid S-oxide, 2,5-dicyano-3,6-bis(N-thiomorpholino)pyrazine S,S-dioxide, indocarbocyaninetetrasulfonate, chloroindocarbocyanine, and 3,6-diaminopyrazine-2,5-dicarboxylic acid.

One of ordinary skill in the art will appreciate that particular optical agents used can depend on the wavelength used for excitation, depth underneath skin tissue, and other factors generally well known in the art. For example, optimal absorption or excitation maxima for the optical agents can vary depending on the agent employed, but in general, the optical agents of the present invention will absorb or be excited by light in the ultraviolet (UV), visible, or infrared (IR) range of the electromagnetic spectrum. For imaging, dyes that absorb and emit in the near-IR (~700-900 nm, e.g., indocyanines) are preferred. For topical visualization using an endoscopic method, any dyes absorbing in the visible range are suitable.

In yet other embodiments, the diagnostic agents can include but are not limited to magnetic resonance (MR) and x-ray contrast agents that are generally well known in the art, including, for example, iodine-based x-ray contrast agents, superparamagnetic iron oxide (SPIO), complexes of gadolinium or manganese, and the like. (See, e.g., Armstrong et al., *Diagnostic Imaging*, 5th Ed., Blackwell Publishing (2004)). In some embodiments, a diagnostic agent can include a magnetic resonance (MR) imaging agent. Exemplary magnetic resonance agents include but are not limited to paramagnetic agents, superparamagnetic agents, and the like. Exemplary paramagnetic agents can include but are not limited to gadopentetic acid, gadoteric acid, gadodiamide, gadolinium, gadoteridol, mangafodipir, gadoversetamide, ferric ammonium citrate, gadobenic acid, gadobutrol, or gadoxetic acid. Superparamagnetic agents can include but are not limited to superparamagnetic iron oxide and ferristene. In certain embodiments, the diagnostic agents can include x-ray contrast agents as provided, for example, in the following references: H. S Thomsen, R. N. Muller and R. F. Mattrey, Eds., *Trends in Contrast Media*, (Berlin: Springer-Verlag, 1999); P. Dawson, D. Cosgrove and R. Grainger, Eds., *Textbook of Contrast Media* (ISIS Medical Media 1999); Torchilin, V. P., *Curr. Pharm. Biotech.* 1:183-215 (2000); Bogdanov, A. A. et al., *Adv. Drug Del. Rev.* 37:279-293 (1999); Sachse, A. et al., *Investigative Radiology* 32(1):44-50 (1997). Examples of x-ray contrast agents include, without limitation, iopamidol, iomeprol, iohexyl, iopentol, iopromide, iosimide, ioversol, iotrolan, iotasul, iodixanol, iodecimol, ioglucamide, ioglunide, iogulamide, iosarcol, ioxilan, iopamiron, metrizamide, iobitridol and iosimenol. In certain embodiments, the x-ray contrast agents can include iopamidol, iomeprol, iopromide, iohexyl, iopentol, ioversol, iobitridol, iodixanol, iotrolan and iosimenol.

Gene Therapy

The nanoparticles of the present invention can also be used to deliver any expressed or expressible nucleic acid sequence to a cell for gene therapy or nucleic acid vaccination. The cells can be in vivo or in vitro during delivery. The nucleic acids can be any suitable nucleic acid, such as deoxyribonucleic acid (DNA) or ribonucleic acid (RNA). Moreover, any suitable cell can be used for delivery of the nucleic acids.

Gene therapy can be used to treat a variety of diseases, such as those caused by a single-gene defect or multiple-gene defects, by supplementing or altering genes within the host cell, thus treating the disease. Typically, gene therapy involves replacing a mutated gene, but can also include correcting a gene mutation or providing DNA encoding for a therapeutic protein. Gene therapy also includes delivery of a nucleic acid that binds to a particular messenger RNA (mRNA) produced by the mutant gene, effectively inactivating the mutant gene, also known as antisense therapy. Representative diseases that can be treated via gene and antisense therapy include, but are not limited to, cystic fibrosis, hemophilia, muscular dystrophy, sickle cell anemia, cancer, diabetes, amyotrophic lateral sclerosis (ALS), inflammatory diseases such as asthma and arthritis, and color blindness.

For general reviews of the methods of gene therapy, see Goldspiel et al., 1993, Clinical Pharmacy 12:488-505; Wu and Wu, 1991, Biotherapy 3:87-95; Tolstoshev, 1993, Ann. Rev. Pharmacol. Toxicol. 32:573-596; Mulligan, 1993, Science 260:926-932; and Morgan and Anderson, 1993, Ann. Rev. Biochem. 62:191-217; May, 1993, TIBTECH 11(5): 155-215. Methods commonly known in the art of recombinant DNA technology which can be used in the present invention are described in Ausubel et al. (eds.), 1993, Current Protocols in Molecular Biology, John Wiley & Sons, NY; and Kriegler, 1990, Gene Transfer and Expression, A Laboratory Manual, Stockton Press, NY.

Formulation and Administration

When the nanocarriers are administered to deliver the cargo as described above, the nanocarriers can be in any suitable composition with any suitable carrier, i.e., a physiologically acceptable carrier. As used herein, the term "carrier" refers to a typically inert substance used as a diluent or vehicle for a drug such as a therapeutic agent. The term also encompasses a typically inert substance that imparts cohesive qualities to the composition. Typically, the physiologically acceptable carriers are present in liquid form. Examples of liquid carriers include physiological saline, phosphate buffer, normal buffered saline, water, buffered water, saline, glycine, glycoproteins to provide enhanced stability (e.g., albumin, lipoprotein, globulin, etc.), and the like. Since physiologically acceptable carriers are determined in part by the particular composition being administered as well as by the particular method used to administer the composition, there are a wide variety of suitable formulations of pharmaceutical compositions of the present invention (See, e.g., Remington's Pharmaceutical Sciences, $17^{th}$ ed., 1989).

Prior to administration, the nanocarrier compositions can be sterilized by conventional, well-known sterilization techniques or may be produced under sterile conditions. Aqueous solutions can be packaged for use or filtered under aseptic conditions and lyophilized, the lyophilized preparation being combined with a sterile aqueous solution prior to administration. The compositions can contain pharmaceutically acceptable auxiliary substances as required to approximate physiological conditions, such as pH adjusting and buffering agents, tonicity adjusting agents, wetting agents, and the like, e.g., sodium acetate, sodium lactate, sodium chloride, potassium chloride, calcium chloride, sorbitan monolaurate, and triethanolamine oleate. Sugars can also be included for stabilizing the compositions, such as a stabilizer for lyophilized compositions.

The nanocarrier compositions can be made into aerosol formulations (i.e., they can be "nebulized") to be administered via inhalation. Aerosol formulations can be placed into pressurized acceptable propellants, such as dichlorodifluoromethane, propane, nitrogen, and the like.

Suitable formulations for rectal administration include, for example, suppositories, which includes an effective amount of a packaged composition with a suppository base. Suitable suppository bases include natural or synthetic triglycerides or paraffin hydrocarbons. In addition, it is also possible to use gelatin rectal capsules which contain a combination of the composition of choice with a base, including, for example, liquid triglycerides, polyethylene glycols, and paraffin hydrocarbons.

Formulations suitable for parenteral administration, such as, for example, by intraarticular (in the joints), intravenous, intramuscular, intratumoral, intradermal, intraperitoneal, and subcutaneous routes, include aqueous and non-aqueous, isotonic sterile injection solutions, which can contain antioxidants, buffers, bacteriostats, and solutes that render the formulation isotonic with the blood of the intended recipient, and aqueous and non-aqueous sterile suspensions that can include suspending agents, solubilizers, thickening agents, stabilizers, and preservatives. Injection solutions and suspensions can also be prepared from sterile powders, granules, and tablets. In the practice of the present invention, compositions can be administered, for example, by intravenous infusion, topically, intraperitoneally, intravesically, or intrathecally. Parenteral administration and intravenous administration are the preferred methods of administration. The formulations of nanocarrier compositions can be presented in unit-dose or multi-dose sealed containers, such as ampoules and vials.

The pharmaceutical preparation is preferably in unit dosage form. In such form the preparation is subdivided into unit doses containing appropriate quantities of the active component, e.g., a nanocarrier composition. The unit dosage form can be a packaged preparation, the package containing discrete quantities of preparation. The composition can, if desired, also contain other compatible therapeutic agents.

In therapeutic use, the nanocarrier compositions including a therapeutic and/or diagnostic agent, as described above, can be administered at the initial dosage of about 0.001 mg/kg to about 1000 mg/kg daily. A daily dose range of about 0.01 mg/kg to about 500 mg/kg, or about 0.1 mg/kg to about 200 mg/kg, or about 1 mg/kg to about 100 mg/kg, or about 10 mg/kg to about 50 mg/kg, can be used. The dosages, however, can be varied depending upon the requirements of the patient, the severity of the condition being treated, and the nanocarrier composition being employed. For example, dosages can be empirically determined considering the type and stage of cancer diagnosed in a particular patient. The dose administered to a patient, in the context of the present invention, should be sufficient to affect a beneficial therapeutic response in the patient over time. The size of the dose will also be determined by the existence, nature, and extent of any adverse side-effects that accompany the administration of a particular nanocarrier composition in a particular patient. Determination of the proper dosage for a particular situation is within the skill of the practitioner. Generally, treatment is initiated with smaller dosages which are less than the optimum dose of the nanocarrier composition. Thereafter, the dosage is increased by small increments until the optimum effect under circumstances is reached. For convenience, the total daily dosage can be divided and administered in portions during the day, if desired.

Loading of Nanocarriers

Loading of the diagnostic and therapeutic agents can be carried out through a variety of ways known in the art, as disclosed for example in the following references: de Villiers, M. M. et al., Eds., *Nanotechnology in Drug Delivery*, Springer (2009); Gregoriadis, G., Ed., *Liposome Technology: Entrapment of drugs and other materials into liposomes*, CRC Press (2006). In some embodiments, one or more therapeutic agents can be loaded into the nanocarriers. Loading of nanocarriers can be carried out, for example, in an active or passive manner. For example, a therapeutic agent can be included during the self-assembly process of the nanocarriers in a solution, such that the therapeutic agent is encapsulated within the nanocarrier. In certain embodiments, the therapeutic agent may also be embedded in the lamellar layer. In alternative embodiments, the therapeutic agent can be actively loaded into the nanocarriers. For example, the nanocarriers can be exposed to conditions, such as electroporation, in which the lamellar membrane is made permeable to a solution containing therapeutic agent thereby allowing for the therapeutic agent to enter into the internal volume of the liposomes.

The diagnostic and therapeutic agents can also be covalently or ionically linked to the surface of the nanocarrier, in the interior of the micelle, or within the lamellar layer of the micelle.

VI. Methods for Disease Treatment

In some embodiments, the present invention provides a method for treating a subject with a disease. The method includes administering a therapeutically effective amount of a particle to the subject. The particle includes from about 20 to about 200 conjugates of the present invention and a therapeutic agent. Thus, the disease is treated.

Any suitable disease can be treated using the conjugates and particles of the present invention. Representative diseases include cancer and Parkinson's disease, among others. Cancers contemplated for treatment using the methods of the present invention include leukemia, lymphoma, skin cancers (including melanomas, basal cell carcinomas, and squamous cell carcinomas), epithelial carcinomas of the head and neck, lung cancers (including squamous or epidermoid carcinoma, small cell carcinoma, adenocarcinoma, and large cell carcinoma), breast cancer, gastrointestinal tract cancers, malignant tumors of the thyroid, sarcomas of the bone and soft tissue, ovarian cancer, carcinoma of the fallopian tube, uterine cancer, cervical cancer, prostatic carcinoma, testicular cancer, bladder cancer, renal cell carcinoma, pancreatic cancer, and hepatocellular cancer. In some embodiments, the present invention provides a method for treating a subject with a cancer characterized by solid tumors. In some embodiments, the disease is selected from the group consisting of a cancer and Parkinsons's disease. In some embodiments, the cancer is *Glioblastoma* multiforme.

In some embodiments, the present invention provides a method for treating a subject with brain cancer. Brain cancers include gliomas, meningiomas, pituitary adenomas, and nerve sheath tumors. In some embodiments, the brain cancer is *Gliobastoma* multiforme. *Gliobastoma* multiforme presents variants including giant cell glioblastoma and gliosarcoma.

Any suitable therapeutic agent is useful in combination with the conjugates and particles of the present invention. In some embodiments, the therapeutic agent is selected from the group consisting of doxorubicin, temzolomide, and rapamycin. In other embodiments, the therapeutic agent is doxorubicin.

VII. Examples

Materials

Fmoc-protected amino acids, 2-(1H-Benzotriazole-1-yl)-1,1,3,3-tetramethyluronium hexafluorophosphate (HBTU), 2-(6-Chloro-1H-benzotriazole-1-yl)-1,1,3,3-tetramethylaminium hexafluorophosphate (HCTU) were purchased from EMD biosciences and used without further purification. The side chain protecting groups of the Fmoc-protected amino acids were as follows: Lys(Boc), Glu(OtBu), Asp (OtBu), Cys(Trt), Arg(Pbf), His(Trt), Trp(Boc), Gln(Trt). In addition, Lys(Fmoc) was used for the conjugation of two palmitic acids to each peptide, and a linker, Fmoc-6-Ahx-OH (Sigma Aldrich) was appended between the peptide and the alkyl tails. Peptide synthesis grade diisopropylethylpropylamine (DIPEA), trifluoroacetic acid (TFA), triisopropylsilane, diethyl ether, HPLC-grade dimethylformamide (DMF), dichloromethane (DCM) and acetonitrile were purchased from Fisher and used without further purification. Piperidine and palmitic acid were purchased from Sigma Aldrich. Negative stain reagent phosphotungstic acid was purchased from Ted Pella and prepared as the 2 wt % stock solution in DI water.

Example 1

Preparation of Conjugates

Figure 23:
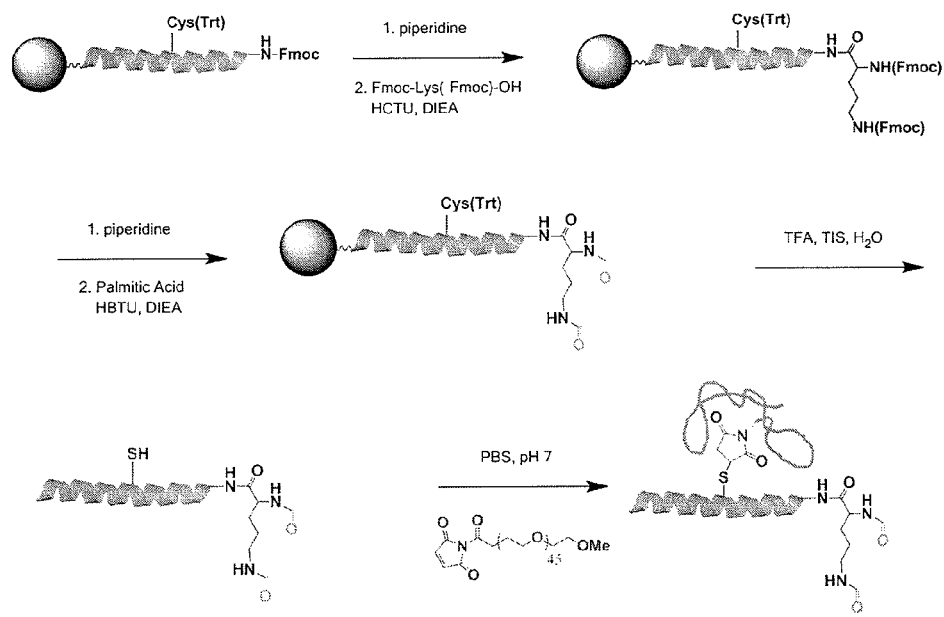
FIG. 23 shows a representative synthetic scheme for the preparation of the amphiphilic peptide polymer conjugates.
Figure 24:
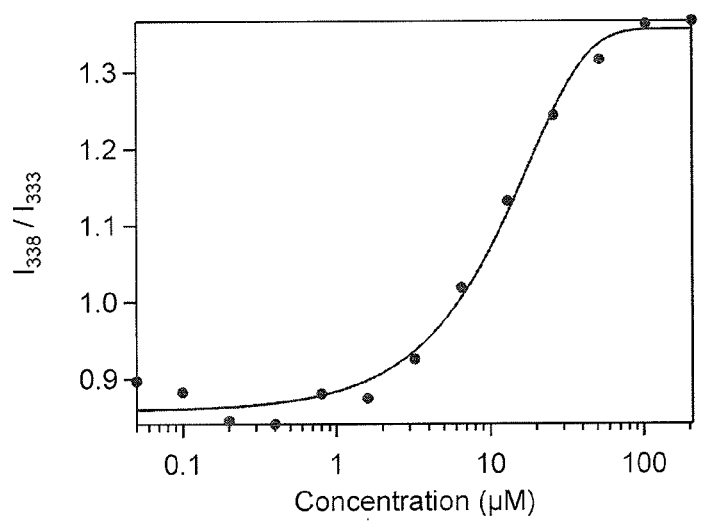
FIG. 24 shows the critical micellar concentration measurement by the pyrene encapsulation method.

The peptides, referred to hereafter as
1CW (EVEALEKKVAALECKVQALEKKVEALEHGW),
BB (GGGEIWKLHEEFLKKFEELLKLHEERLKKM),
SR (EGKAGEKAGAALKCGVQELEKGAEAGEGGW), and
1coi-W (EVEALEKKVAALESKVQALEKKVEALEHGW), were previously described in detail. The C-terminus of peptides can be prepared with GGG, HHH, KK, EE, RGD and AYSSGAPPMPPF, and combinations thereof, and other peptide sequences through Fmoc-solid phase synthesis. The scheme in FIG. 23 is typical of the procedures used for conjugate synthesis.

The peptides were synthesized on a Protein Technologies Prelude solid phase synthesizer using standard 9-fluorenylmethyl carbamate (Fmoc) protection chemistry on Wang resin (Nova Biochem), typically at 0.05 mmol scale. The side chain protecting groups were as follows: Lys(Boc), Glu(OtBu), Asp(OtBu), Cys(Trt), Arg(Pbf), His(Trt), Trp-(Boc), Ser(tBu), Gln(Trt). Peptides synthesized with additional residues appended to the C-terminus optionally include an interstitial GGG linking sequence. For the synthesis of 1CW-PEG conjugates, the serine at position 14 was mutated to cysteine to facilitate conjugation of maleimide end-functionalized PEG. Similarly for BB, the lysine at position 15 was mutated to cysteine. For the synthesis of dC16-1CW-P2K, Fmoc-hexanoic acid was attached between the peptide and fatty acid as a linker. Fmoc-Lys(Fmoc)-OH was then appended to the N-terminus to allow simultaneous coupling of palmitic acid to the amine of the lysine side chain and the N-terminus of the peptide, thus yielding a double alkane tail, and the cysteine at position 15 was used for coupling of maleimide-functionalized PEG of molecular weight 2000 g/mol and 5000 g/mol (Rapp Polymere) to the middle of the peptide sequence. tC16-1CW-P2K was synthesized with two consecutive rounds of coupling with Fmoc-Lys(Fmoc)-OH at the N-terminus generating four branching points to attach palmitic acids. For peptide 9, prior to peptide cleavage from the resin, the N-terminus was acetylated using a 1:1 (v/v) acetic anhydride: pyridine solution for 30 min. The peptides were cleaved from the resin and simultaneously deprotected using 90:8:2 trifluoroacetic acid (TFA)/ethanedithiol/water for 3.5 h. Crude peptides were precipitated in cold ether and subsequently dissolved in water and lyophilized. Maleimide end-functionalized PEG, purchased from Rapp Polymere (Germany), was then coupled to the cysteine residues of the peptides, which were in white powder form, in 25 mM potassium phosphate buffer at pH 8 for 1 h. 3 PEGs of three varying molecular weights were utilized: 750, 2000, and 5000 Da. These are referred henceforth as PEG750, PEG2K, and PEG5K, respectively.

For preparation of BB-PEG conjugates, the lysine at position 15 was mutated to cysteine to facilitate coupling of maleimide-functionalized PEG of molecular weight 2000 g/mol and 5000 g/mol (Rapp Polymere) to the Middle of the peptide sequence. Peptides were synthesized on a Protein Technologies Prelude solid phase synthesizer using standard 9-fluorenylmethyl carbamate (Fmoc) protection chemistry on PEG-PAL resin (Applied Biosystems), typically at 0.05 mmol scale. Peptides were dissolved in phosphate buffer (25 mM, pH=8) at a concentration of 10 mg/ml. The solution was purged with nitrogen for 5 mins before the addition of maleimide functionalized polyethylene glycol. PEG-maleimide was added in 7-8 equivalents of the peptides. The mixture was stirred at room temperature for at least overnight before HPLC purification.

The di-lipid conjugate dC16-1CW-P2K was prepared by reacting Fmoc-hexanoic acid was attached between the peptide and fatty acid as a linker. Fmoc-Lys(Fmoc)-OH was then appended to the N-terminus to allow simultaneous coupling of palmitic acid to the amine of the lysine side chain and the N-terminus of the peptide, thus yielding a double alkane tail. Crude conjugates were precipitated in cold ether and subsequently dissolved in solution and lyophilized, resulting in a white powder.

The tetra-lipid conjugate tC16-1CW-P2K was synthesized with two consecutive rounds of coupling with Fmoc-Lys(Fmoc)-OH at the N-terminus generating four branching points to attach palmitic acids. Peptides were cleaved from the resin and simultaneously deprotected using 90:8:2 trifluoroacetic acid (TFA)/ethanediol/water for 3.5 hr.

Peptides were also synthesized on a Protein Technologies Prelude solid phase synthesizer using standard 9-fluorenylmethyl carbamate (Fmoc) protection chemistry on PEG-PAL resin (Applied Biosystems), typically at 0.05 mmol scale. Fmoc-Lys(Fmoc)-OH (EMD Bioscience) was appended to the N-terminus to allow coupling of two palmitic acid molecules to the N-terminus of the peptide. Palmitoylated peptides were cleaved from the resin and simultaneously deprotected using 90:8:2 trifluoroacetic acid (TFA)/ethanedithiol/water for 3.5 hr. Crude peptides were precipitated in cold ether and subsequently dissolved in solution and lyophilized, resulting in a white powder. Cysteine at position 14 facilitates the site-specific coupling of maleimide-functionalized PEG of molecular weight 2000 g/mol or 5000 g/mol (Rapp Polymere) to the middle of the peptide sequence.

Conjugates 1, 3, 5-6, 8 10-12, and 14-16 were prepared by the method above. No additional amino acids were used for conjugates 14-16. Conjugate 2 was prepared as described above, without the step of attaching the polymer to the peptide. Conjugate 4 was prepared by coupling palmitic acid to the N-terminus of the peptide without the interstitial Fmoc-Lys(Fmoc)-OH residue. Conjugate 13 was by coupling palmitic acid to the N-terminus of the peptide without interstitial aminohexanoic acid and Fmoc-Lys(Fmoc)-OH residues.

Conjugate 7 was prepared by the following method: carboxyl terminated polybutadiene (PBD, Polymer source) was dissolved in mixture of dichloromethane and dimethyl formamide. In the presence of HCTU and DIPEA, PBD was reacted with the amino group at the N-terminus of the peptide (1-CW) through solid phase synthesis. Upon completion of coupling reaction between PBD and peptide, the conjugate was cleaved with 95% TFA, 2.5% TIS and 2.5% H2O for 1 hour. The crude PBD-1CW was purified by HPLC and characterized by MALDI.

Figure 11:
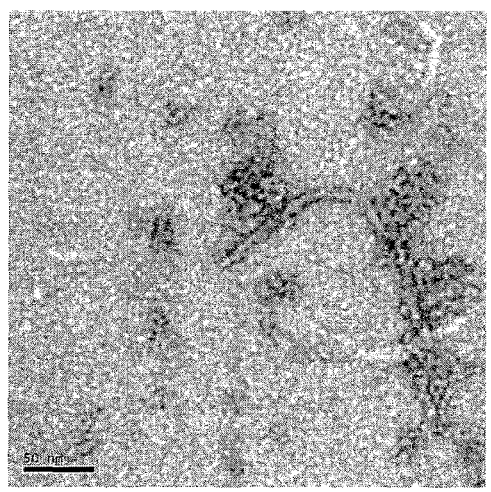
FIG. 11A shows a TEM image of the particles prepared from the PS-BB (side functionalization) conjugate 9.
FIG. 11B shows the MALDI-TOF of the PS-BB conjugate 9.
Figure 11:
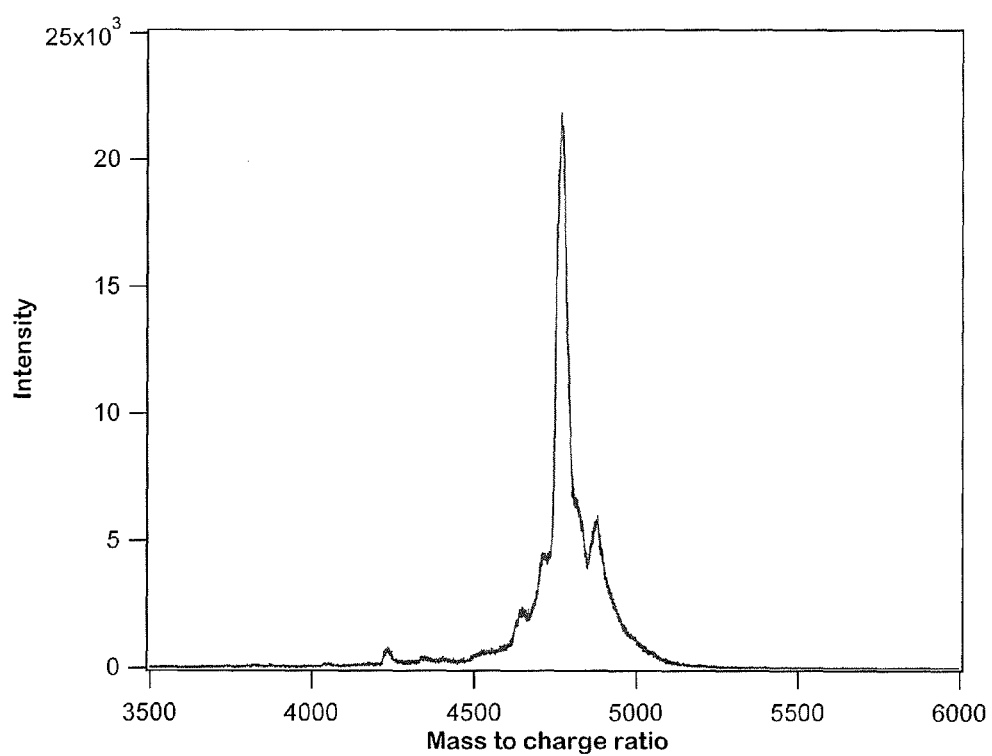
Figure 12:
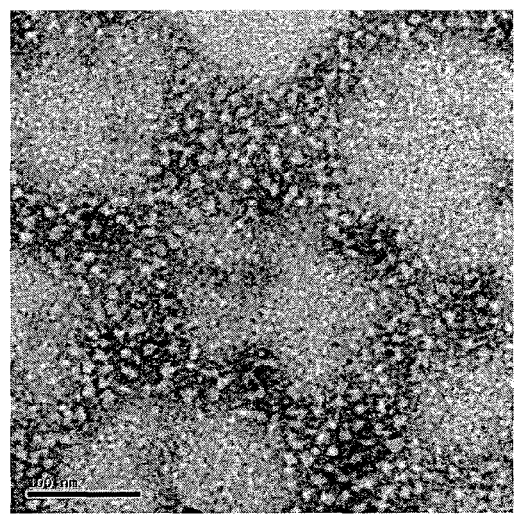
FIG. 12A shows a TEM image of the particles prepared from the sC14-1CW-P2K-DGR conjugate 13.
FIG. 12B shows the small-angle X-ray scattering (SAXS) of the particles prepared from the sC14-1CW-P2K-DGR conjugate 13 at 16 wt. %.
FIG. 12C shows the MALDI-TOF of the sC14-1CW-P2K-DGR conjugate 13.
Figure 12:
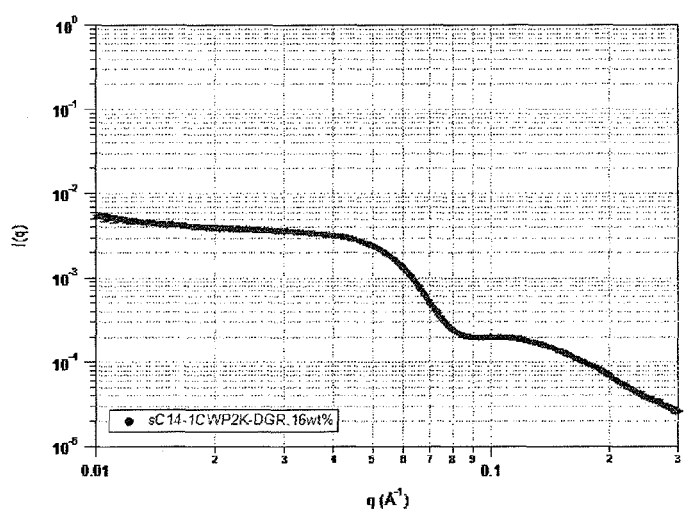
Figure 12:
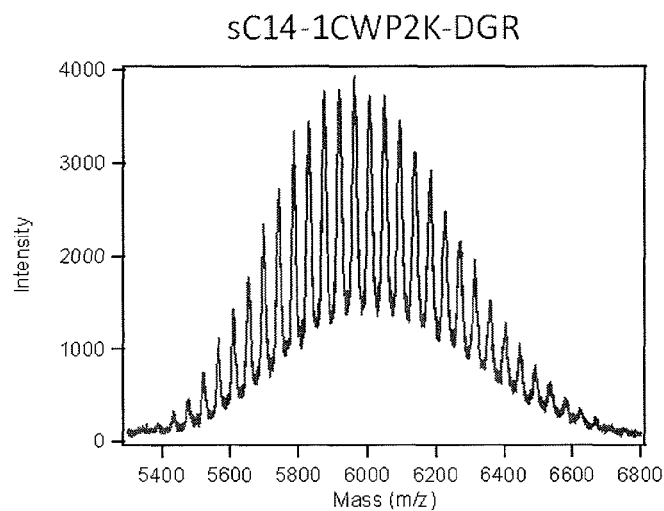
Figure 13:
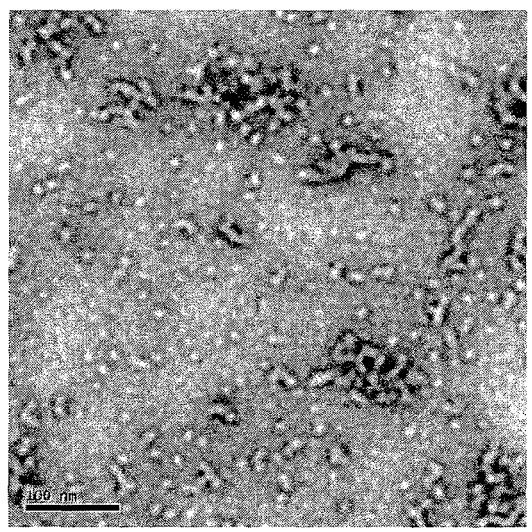
FIG. 13A shows a TEM image of the particles prepared from the sC16-1CW-P2K-KK conjugate 4.
FIG. 13B shows the small-angle X-ray scattering (SAXS) of the particles prepared from the sC16-1CW-P2K-KK conjugate 4 at both 4 wt. % (lower on the right) and 16 wt. % (upper on the right)
FIG. 13C shows the MALDI-TOF of the sC16-1CW-P2K-KK conjugate 4.
Figure 13:
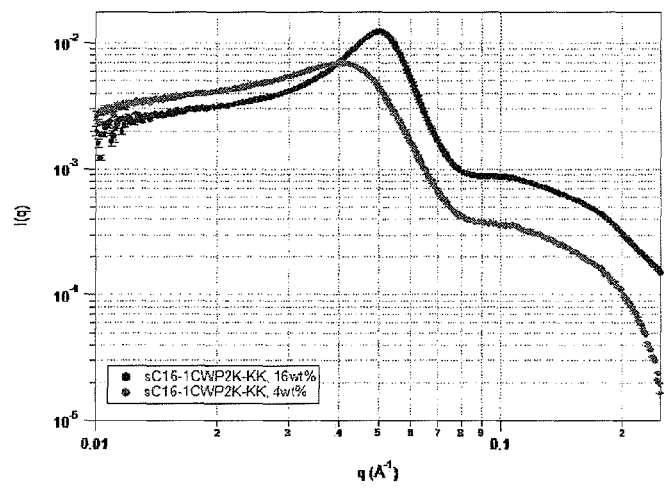
Figure 13:
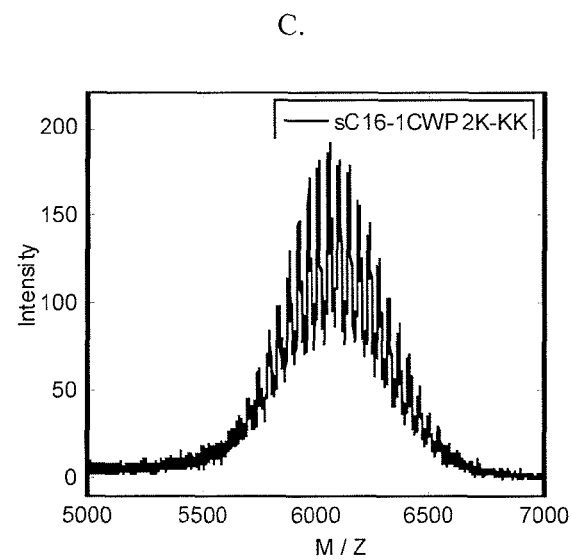
Figure 14:
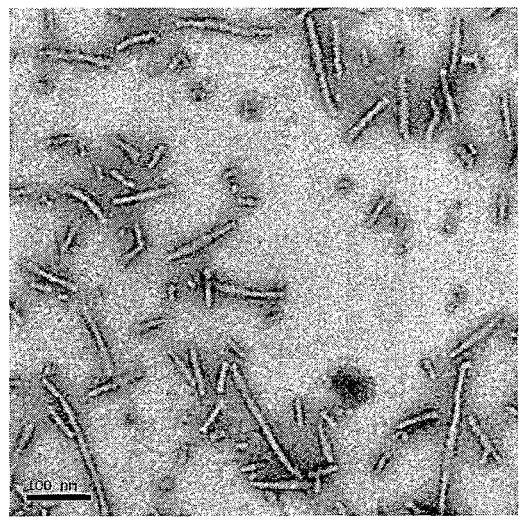
FIG. 14A shows a TEM image of the particles prepared from the tC16-1CW-P2K-KK conjugate 6.
FIG. 14B shows the MALDI-TOF of the tC16-1CW-P2K-KK conjugate 6.
Figure 14:
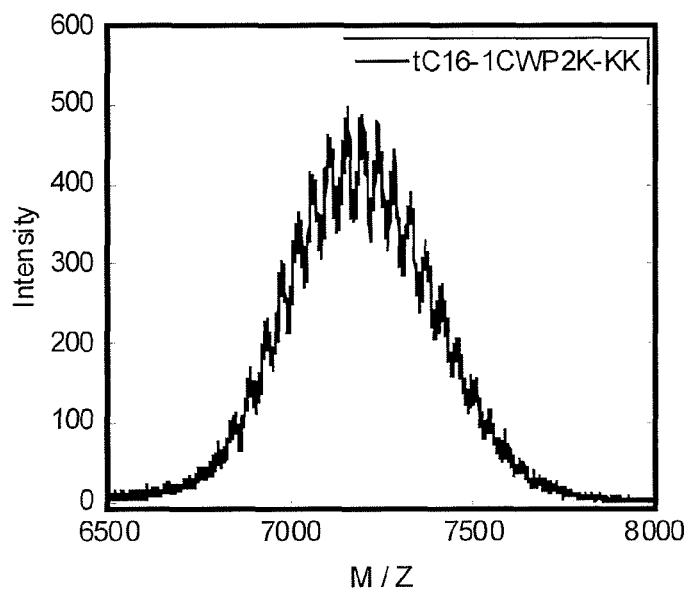
Figure 15:
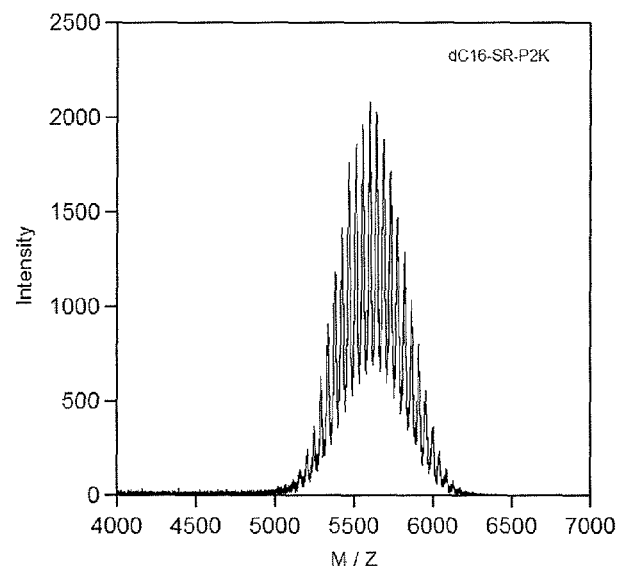
FIG. 15 shows the MALDI for the dC16-SR-PEG2k conjugate 14.
Figure 16:
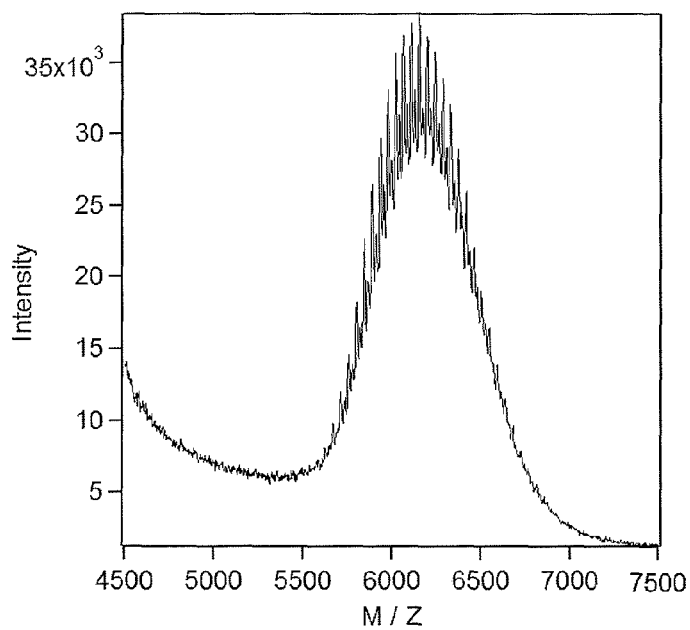
FIG. 16 shows the MALDI for the dC18-1CW-PEG2k conjugate 15.
Figure 17:
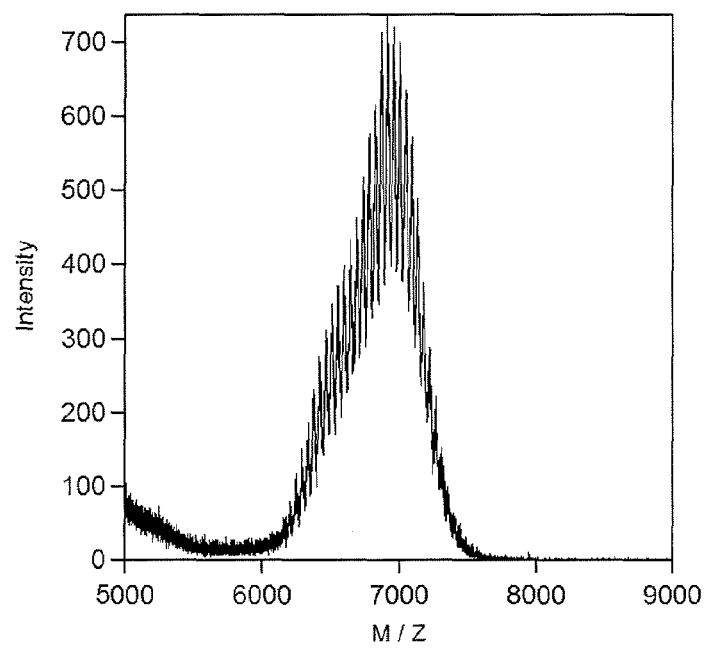
FIG. 17 shows the MALDI for the dC16-1CW-P2K-$KKK_{F1}$ conjugate 17.

Conjugate 9 was prepared using BB with polystyrene on its side by first preparing peptide such that it could be selectively deprotected to result in free amino groups which could be utilized for coupling carboxy terminated polymers to the peptide chain. More specifically, Allyloxycarbonyl (Alloc) protected lysine, Lys(Alloc), was used as the amino acid at 15$^{th}$ position of the peptide chain. The removal of Alloc group was accomplished by utilizing palladium catalyst. Resin bound peptide with the N-terminus acylated as above was treated with tetrakis (triphenylphosphine) palladium(0) Pd(PPh$_3$)$_4$ catalyst and radical trapping agent PhSiH$_3$ in DCM. The reaction was repeated two more times. In the next step, the resulting free amino groups of lysine were utilized for conjugating carboxy terminated polymer using HCTU/DIPEA chemistry. The reaction was performed at room temperature for 48 hours. Polymer reacted resin was cleaved and deprotected and the cleaved mixture was precipitated in cold diethyl ether and purified by RP-HPLC. MALDI of the BB-PS conjugate is shown in FIG. 11B. The molecular weight of the conjugate was found to be 4720 Da.

Conjugates 17 and 18 were prepared by incorporating allyloxycarbonyl (Alloc) protected lysine, Lys(Alloc), as the first amino acid at the C-terminus of the peptide chain. Following acylation of the N-terminus with linking groups and palmitic acid as described above, the removal of the Alloc group was accomplished by utilizing palladium catalyst. Resin bound peptide was treated with tetrakis (triphenylphosphine) palladium(0) Pd(PPh$_3$)$_4$ catalyst and radical trapping agent PhSiH$_3$ in DCM. The reaction was repeated two more times. In the next step, the resulting free amino groups of lysine were utilized for conjugating carboxy terminated fluorescein using HCTU/DIPEA chemistry. The reaction was performed at room temperature for 12 hours and repeated twice. The resin was cleaved and the cleaved mixture was precipitated in cold diethyl ether. The crude fluorescein labeled peptide was reacted with maleimide end functionalized PEG2000 in phosphate buffer (pH=7.4) for overnight. The mixture was purified by HPLC.

Example 2

Self-Assembly of Conjugates to Form Helix Bundles

Prepared as previously described in J. Y. Shu, C. Tan, W. F. DeGrado, T. Xu, *Biomacromolecules,* 2008, 9(8), 2111-2117. The peptide sequences are selected such that they form helix bundles instantaneously upon dissolving them in aqueous buffered solution.

Example 3

Self-Assembly of Helix Bundles to Form Nanoparticles

Lyophilized peptide-polymer conjugates were dissolved in phosphate buffer (pH=8) at a concentration of 10 mg/ml (~1.5 mM). Upon sonication for 30 s, solutions were diluted to 1 mg/ml (0.15 mM) or 0.1 mg/ml in phosphate buffer (pH=8). 5 µl of the diluted peptide solution were applied to a discharged holey carbon-coated copper grid (Ted Pella Cu 400 mesh 01824) for 4 minutes before absorbing off excess solution using filter paper (Whatman filter paper 1). The sample on the grid was negatively stained with a 5 µl 2% (w/v) phosphotungstic acid (adjusted to pH=3.3 with 1 M NaOH) for 2 minutes. Excess stain solution was wicked off. After complete drying, grids were examined by TEM at 120 kV (Philips/FEI Tecnai 12).

Example 4

Preparation of dC18-1CW-P2K (15)

Figure 18:
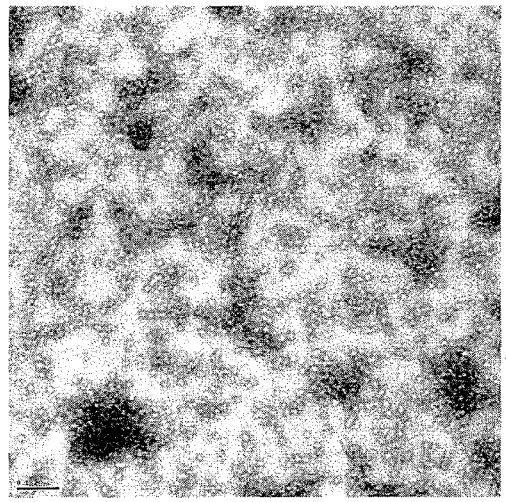
FIG. 18 shows the TEM of spherical nanoparticles prepared from the dC18-1CW-P2K conjugate 15 (FIG. 18A) with similar size to those prepared from the dC16-1CW-P2K conjugate 16. However, DSC study (FIG. 18B) showed a much higher transition temperature for the longer lipid chain with 35° C., compared with 17° C. for particles prepared from the dC16-1CW-P2K conjugate 16.
Figure 18:
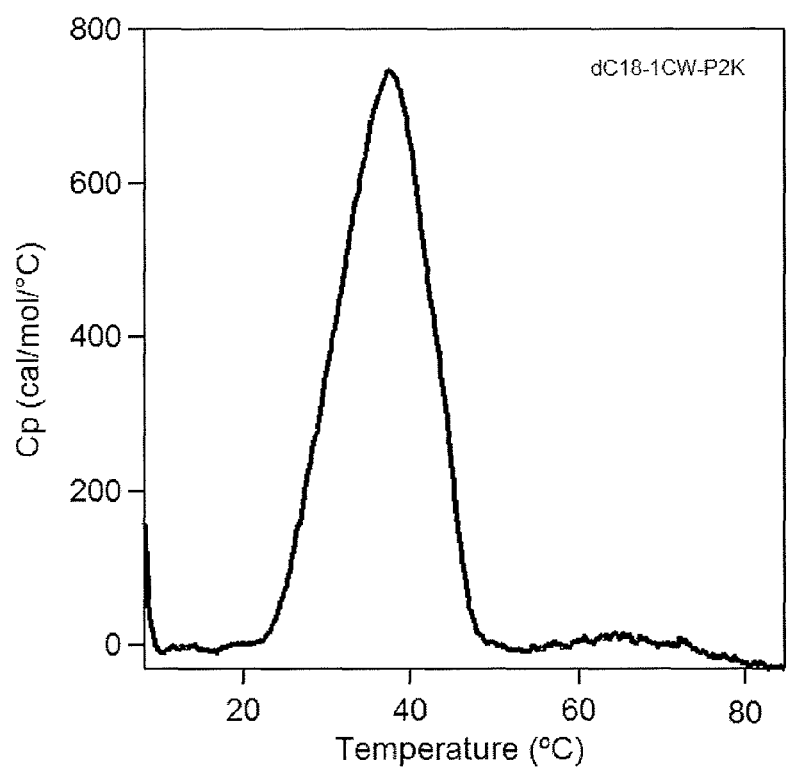

To construct nanoparticles with more compact lipid packing within hydrophobic core above room temperature, a new peptide-polymer conjugate was prepared with two stearic acid chains attached at the N-terminus of 1CW (referred as dC18-1CW-P2K, Conjugate 15). TEM (FIG. 18A) showed the formation of spherical nanoparticles with similar size to dC16-1CW-P2K. However, DSC study (FIG. 18B) showed a much higher transition temperature for the longer lipid chain with 35° C., compared with 17° C. for dC16-1CW-P2K. No additional amino acids were attached at the C-terminus. TEM shows particles size about ~15 nm in diameter.

Example 5

Characterization of Nanoparticles

Methods
Reversed-Phase High-Pressure Liquid Chromatography (RP-HPLC).

The amphiphilic conjugates were purified using RP-HPLC (Beckman Coulter) on a C4 column (Vydac). The flow rate was 10 ml/min for semi-preparative runs and conjugates were injected at a concentration of 10 mg/ml. Elution was monitored with a diode array detector at wavelengths of 220 nm and 280 nm. Conjugates were eluted with a linear AB gradient, where solvent A consisted of water plus 0.1% (v/v) TFA and solvent B consisted of acetonitrile plus 0.1% (v/v) TFA. A linear gradient of 30 to 100% B over 30 min was used, with typical elution ~85% B. Purification yield is ~40%.

MALDI-TOF Spectrometry.

The identity and purity of the peptides were verified by MALDI-TOF mass spectrometry using α-cyano-4-hydroxycinnamic acid matrix. Mass spectra were recorded on an Applied BioSystems Voyager-DE Pro.

Critical Micelle Concentration (CMC).

The pyrene solubility method was used to determine the critical micelle concentration. A saturated solution of pyrene in PBS (~6×10$^{-7}$ μM) was prepared and used to dissolve the samples. Fluorescence spectra were collected using a Jasco FP-6500 spectrofluorometer with a bandwidth of 0.5 mm for both excitation and emission. For fluorescence excitation spectra, $\lambda_{em}$ was 390 nm. When solubilized in aqueous media at low peptide-polymer conjugate concentrations, pyrene exhibits an excitation peak ~333 nm. As the concentration of the amphiphilic conjugate increases such that micelles form, the peak at ~333 nm shifts to ~338 nm, which corresponds to the excitation of pyrene that has been incorporated into the hydrophobic core of the micelles. The ratio of the peaks at 338 and 333 nm was plotted to determine the cmc, which corresponds to the intersection of the linear extrapolations of the first two slopes in the data set.

Cryo Transmission Electron Microscopy.

Cryo sample preparation was done on a Vitrobot (FP5350/60). 5 μl of peptide solution were pipetted on a holey carbon grid and blotted for 2 s to remove excess solution. The sample was quickly plunged into liquid ethane and transferred to a cryo holder containing liquid nitrogen. Samples were imaged on a JEOL 4000 microscope at −177° C. using low dose conditions.

Negatively Stained Transmission Electron Microscopy.

Lyophilized peptide powder was dissolved at 1 mg/ml in 25 mM phosphate buffer at pH 7.4. 5 μl of peptide solution was dropped on a discharged holey carbon coated grid (Ted Pella 01824). After removing excess peptide solution, 5 μl of phosphotungstic acid (2 wt %, pH=3.3) solution was then applied for 2 minutes. Samples were dried in air and examined by a FEI Tecnai 12 transmission electron microscope at 120 kV.

Small Angle X-ray Scattering (SAXS).

SAXS was carried out at beamline 7.3.3 at the Advanced Light Source, Lawrence Berkeley National Laboratory. Samples were dissolved in 25 mM $KH_2PO_4$, pH 7.4 buffer at a range of concentrations, from 0.5 wt % to 16 wt %. Samples of the lowest concentration were measured in a homemade circulating flow cell with 0.025 mm thick muscovite mica widows and counted for 5 s 50 times to garner the form factor (Lipfert et al., *Rev. Sci. Instrum.* 77, (2006)). Samples of higher concentration were measured in 2 mm boron-rich thin-walled capillary tubes to investigate both the form and structure factors. In-situ temperature studies were performed using a capillary holder connected to a peltier device. Samples were heated from 25° C. to 85° C. at a ramp rate of 1° C./min and held for 1 min to ensure equilibrium before acquisition of 10 images of 5 s exposures. The sample to detector distance was ~1.7 m, providing a q range of 0.01 to 0.3 Å$^{-1}$, where q=4π sin(θ/2)/λ, θ=scattering angle, and λ=1.24 Å. The x-ray energy was 10 keV. Scattering was collected with a PILATUS detector. 2D diffraction patterns were radially integrated to garner a 1D profile of the scattering intensity. Form factors were fit using the core-shell sphere model included in the SANS software analysis package provided by National Center for Neutron Research at National Institute of Standards and Technology (NCNR-NIST). In more detail, form factors were fit to a core-shell sphere model that includes a Gaussian distribution in overall size of the micelle. Data were fit with a limited q range between 0.04 and 0.15 Å$^{-1}$ in order to garner the best fit in the q range of interest. There appears to be a slight decrease in micellar size over the first 16 hrs, as seen in the shift in the scattering minimum at q ~0.06 Å$^{-1}$, possibly due to aging of the micelles towards better subunit packing. SAXS results confirmed exceptional long-term stability of micelles, as there is no aggregation or increases in micelle sizes over the course of 2 months.

Small Angle Neutron Scattering (SANS).

SANS of micelles was carried out at beamline CG-3 at High Flux Isotope Reactor, Oak Ridge National Laboratory. Samples were dissolved in 25 mM $KH_2PO_4$, pH 7.4 buffer at 5 mg/ml and measured in 1 mm pathlength cylindrical cuvettes holding a sample volume of ~300 μl. The sample to detector distance was ~1.1 m, providing a q range of 0.01 to 0.3 Å$^{-1}$, where q=4π sin(θ/2)/λ, θ=scattering angle, and λ=6 Å. Scattering was collected for 60 min on a 2D $^{3}$He detector and diffraction patterns were radially integrated to garner a 1D profile of the scattering intensity. Form factors were fit using a core-shell model with interfacial widths (Berndt et al., *Angew. Chem. Int. Ed.*, 45:1737-1741 (2006)). Fitting of the data to a core-shell spherical form factor with interfacial widths allowed estimation of the specific volume of the micelle to be 0.877 ml/g.

Analytical Ultracentrifugation.

Sedimentation equilibrium experiments were performed on a Beckman Optima XL-A at 25° C. with samples solubilized in 25 mM phosphate at pH 7.4. The path length of the cells was 1.2 cm and the An-60Ti rotor was used. Measurements at 5000, 7000, and 10000 rpm were taken after 10 h of spinning at each speed to ensure equilibrium, which was verified by matching the early and late data sets. The radial distribution of absorbance was monitored at 280 nm. Sample concentrations were 100 μM, and sample volumes were 120 μl. The specific volume of 1CW-dC16-P2K was estimated to be 0.877 ml/g using the software Sednterp (http://www.jphilo.mailway.com) and relying on the fit of the SANS profile of 1CW-dC16-P2K to a core-shell model with interfacial widths (FIG. S4) to estimate the number of water molecules that penetrate the shell of the micelle. The density of the buffer was 1.004 g/ml. Nonlinear global fits were made using the UltraScan software program (http://www.ultrascan.uthscsa.edu/).

Dynamic Light Scattering (DLS).

DLS size measurements were taken on a Malvern Zetasizer Nano-ZS with a 633 nm laser and a scattering angle of 17° to determine the hydrodynamic radius of samples in solution. Samples were passed through 0.22 μm filters prior to the measurements.

Size Exclusion Chromatography (SEC).

SEC was carried out on a BioSep-SEC-S 3000 column (Phenomenex). The flow rate was 1 ml/min with 25 mM phosphate buffer (pH=7.4) as the elution solvent. The elution profile was monitored with a UV-vis detector at wavelengths of 220 nm and 280 nm. The elution volume of the self-assembled nanoparticles composed of 1CW-dC16-P2K is ~6.5 ml, corresponding to that of protein standards with a MW of 670 kDa.

Circular Dichroism (CD).

Temperature dependent CD measurements were made on a Jasco J810 spectropolarimeter. CD spectra were collected from 260 to 190 nm at 0.2 nm intervals, a rate of a 100 nm/min, a response time of 4 s, and a bandwidth of 1 nm. Temperature melt curves were measured using ~200 μM solutions. The ellipticity was monitored at 222 nm as the temperature increased from 5° to 95° C. in 5° C. increments at a rate of 1° C./min, with a 1 min equilibration time at each temperature before the measurement was taken. One hundred percent helicity was estimated using the formula $$[\theta]_{222}=40,000-[1-(2.5/n)].$$

Temperature dependent circular dichroism shows that peptides maintain high helicity in the temperature range of 25° C. to 85° C. from 74-55%. For comparison, peptides without lipid chain attached unfold significantly showing only ~20% helicity upon heating to 85° C. (see, e.g., Forood et al., *Proc. Natl. Acad. Sci. U.S.A.*, 90:838-842 (1993); Chen et al., *Biochemistry*, 13: 3350-3359 (1974)). Circular dichroism spectra of SR-dC16-PEG2K and 1CW-dC16-PEG2K. SR-dC16-PEG2K forms predominantly a random coil, with a helical content of less than 5%, as compared to 1CW-dC16-PEG2K, which has a helical content of 74% under the same conditions. This confirms that the scrambled peptide sequence adopts a mostly random coil conformation, as designed.

Differential Scanning calorimetry (DSC).

DSC was performed on a VP-MicroCal calorimeter (GE). ~600 µl of sample and buffer were loaded into two parallel stainless steel cells that were sealed tightly under the pressure of ~27 psi to prevent water evaporation during the heating cycle. The temperature was increased from 5° to 85° C. at a rate of 1° C./min, with a 15 min equilibration time at 5° C. DSC thermograms were obtained after concentration normalization and baseline correction using the Origin software provided by the MicroCal.

Dynamics of Subunit Exchange Using Self-Quenching Dye-labeled Micelles.

Fluorescein-labeled nanoparticles (donor) were prepared at a concentration of 16 µM in 25 mM phosphate buffer at pH 7.4. Non-labeled nanoparticles (acceptor) were prepared at a concentration of 3.6 mM using the same buffer. The two solutions were mixed in a 5:1 volume ratio, giving a donor:acceptor molar ratio of 1:40. Time dependent fluorescence intensity was recorded every 30 seconds upon mixing, with the excitation wavelength at 488 nm and emission at 527 nm.

Förster Resonant Energy Transfer (FRET).

A lipophilic FRET pair, 3,3'-dioctadecyloxacarbocyanine perchlorate (DiO, donor) and 1,1'-dioctadecyl-3,3,3',3'-tetramethylindocarbocyanine perchlorate (DiI, acceptor) were used to measure the energy transfer upon mixing. DiO and DiI were dissolved in acetone to a concentration at 0.1 mg/ml, respectively. 50 µl DiO and 50 µl DiI were independently added to 0.5 ml of peptide aqueous solution (1 mg/ml, pH=7.4). After 24 hours stirring at room temperature, acetone was evaporated with vials left open for 24 hours. The solutions were then subject to centrifugation and spin dialysis to remove any insoluble aggregates and soluble dyes in the supernatant. The resulting dye-encapsulated nanoparticles were characterized by size exclusion chromatography. Encapsulation of dye molecules within nanoparticles were confirmed by the overlap of elution profiles monitored at 220 nm and 490 nm, respectively for DiO, at 220 nm and 560 nm, respectively for DiI. Time dependent fluorescence intensity was recorded for 44 hours upon mixing the nanoparticle solutions with excitation wavelength at 488 nm.

Elastic Energy Estimation.

In order to estimate the elastic energy stored in the PEG chains when compressed in the confined geometry of the micelle shell, we modeled the polymer chains to be elastic springs described by an elastic spring constant, $\kappa=3k_B T/(Nb^2)$, where $k_B$ is the Boltzmann constant, N is the number of Kuhn monomers, and b is the Kuhn length. The elastic energy is taken to be $U=\frac{1}{2}\kappa x^2$, where x is the difference in radius between a PEG chain compressed in the shell and that of an unperturbed PEG chain free in solution. The radius of gyration of PEG of molecular weight of 2000 Da in aqueous solution is tabulated to be ~1.4 nm. The radius of gyration of PEG in the micelle was estimated to be ~0.5 nm by comparing the conical volume available to each PEGylated 3-helix bundle subunit and the volume occupied by the coiled-coil alone. Both were measured using small angle x-ray scattering and small angle neutron scattering. This yielded a stored elastic energy of ~10 kcal/mol of particle.

Results

Lyophilized peptide-polymer conjugates were dissolved in phosphate buffer (pH=8) at a concentration of 10 mg/ml (~1.5 mM). Upon sonication for 30 s, solutions were diluted to 1 mg/ml (0.15 mM) or 0.1 mg/ml in phosphate buffer (pH=8). 5 µl of the diluted peptide solution were applied to a discharged holey carbon-coated copper grid (Ted Pella Cu 400 mesh 01824) for 4 minutes before absorbing off excess solution using filter paper (Whatman filter paper 1).

Figure 19:
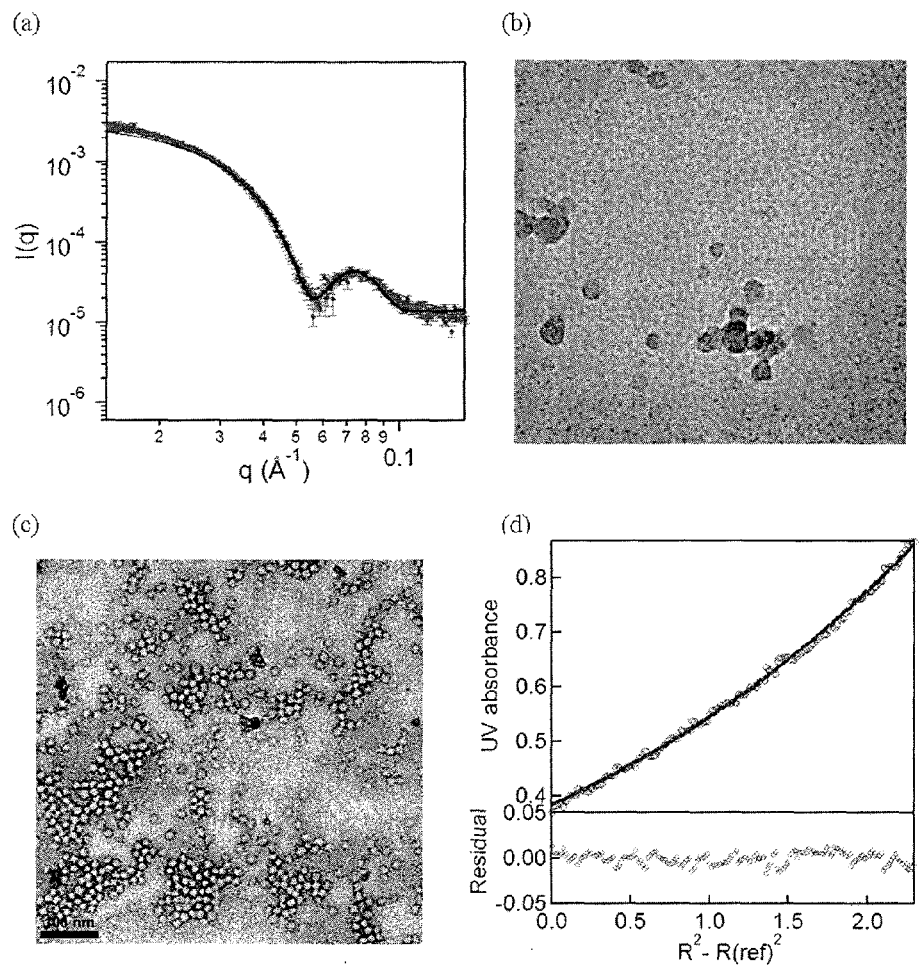
FIG. 19 shows the solution small angle x-ray scattering analysis of the peptide amphiphile based-micelles.
Figure 25:
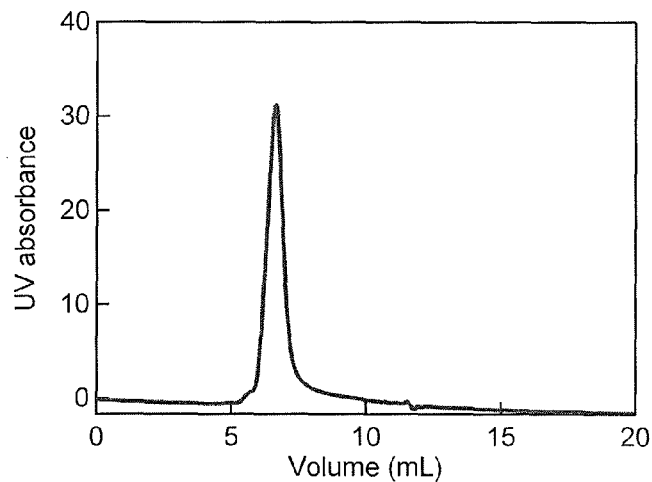
FIG. 25 shows the size exclusion chromatography of samples prepared from the dC16-1CW-P2K conjugate 16 at 1 mg/ml in 25 mM phosphate buffer (pH=7.4).
Figure 26:
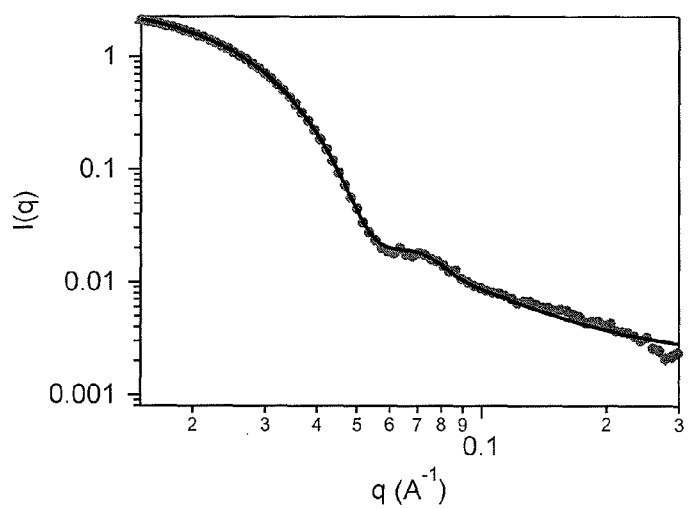
FIG. 26 shows the small angle neutron scattering of samples prepared from the dC16-1CW-P2K-HHH conjugate 1 with deuterated alkyl tails, at 5 mg/ml in 25 mM pH 7.4 $D_2O$ phosphate buffer. Based on best fit analysis of the data, the specific volume of the micelle was estimated to be 0.877 ml/g.

Using the pyrene solubility method (Astafieva et al., *Macromolecules*, 26:7339-7352 (1993)), the critical micelle concentration (CMC) of 1CW-dC16-PEG2K was found to be 4 µM, comparable to other peptide amphiphile systems (Mackay et al., *Nat. Mater.*, 8: 993-999 (2009). Above the CMC, dC16-1CW-P2K-HHH forms uniform micelles. Solution small angle x-ray scattering (SAXS) experiments (FIG. 19A) indicate the formation of core-shell spherical micelles, ~15 nm in diameter. The C16 alkyl tails form the hydrophobic core, ~3.8 nm in diameter, and the 1CW-PEG2K conjugates form a ~5.7 nm thick hydrophilic shell. FIGS. 19B and C show the cryo-TEM image and the TEM image of negatively stained dried nanoparticles, where micellar nanoparticles can be clearly seen. The aggregation number is 78 which corresponds to 26 trimolecular subunit per micelle, as determined by the analytical ultracentrifugation (AUC) results in FIG. 19D and was further confirmed with size exclusion chromatography (SEC) (see FIG. 25) for similar conjugates dC16-1CW-PEG2K.

1CW-dC16-PEG2K forms micelles spontaneously over a wide range of amphiphile concentrations by simply dissolving the lyophilized amphiphile in aqueous media. FIG. 20A shows a series of SAXS profiles of 1CW-dC16-PEG2K solutions with concentrations ranging from 0.5-16 wt %. Scattering profiles at q>0.08 Å$^{-1}$ can be fit to a spherical core-shell model, similar to that shown in FIG. 19A, confirming the integrity of individual micelle and absence of random aggregates. As the volume fraction of micelle increases to 34 vol % at 16 wt % of dC16-1CW-PEG2K, the micelles start to co-assemble into structures with liquid-like ordering reflected by the broad diffraction peak at q ~0.035 Å$^{-1}$ that corresponds to an inter-particle distance of ~18 nm.

Figure 27:
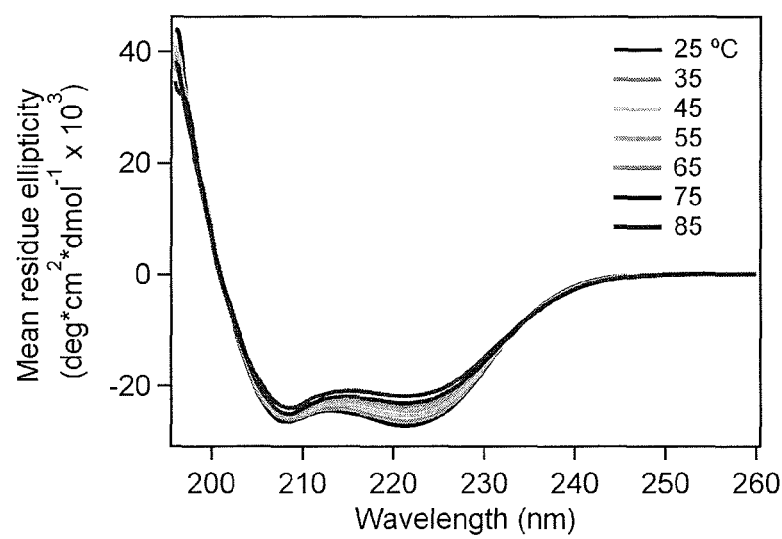
FIG. 27 displays temperature dependent circular dichroism analysis of samples prepared from the dC16-1CW-P2K conjugate 16. The data shows that the peptides maintain high helicity in the temperature range of 25° C. to 85° C. from 74-55%.
Figure 28:
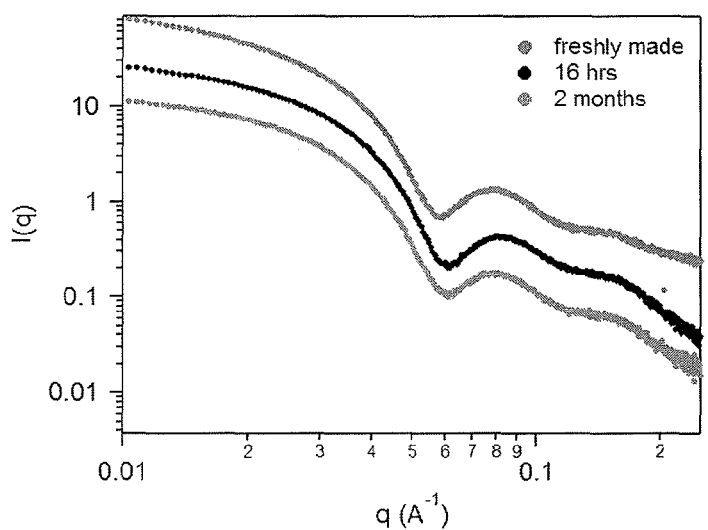
FIG. 28 shows SAXS profiles of samples prepared from the dC16-1CW-P2K conjugate 16 that were freshly made (top line) and incubated at 20° C. for 16 hrs (middle line) and 2 months (bottom line).
Figure 29:
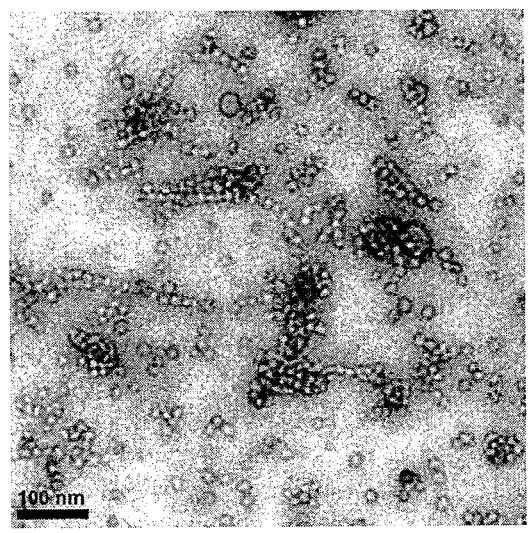
FIG. 29 shows a negatively stained TEM of the dC16-1CW-P2K-HHH conjugate 1 in phosphate buffer (pH=7.4) stored at room temperature for 9 months, showing a major fraction of spherical micelles with ~15 nm in diameter.

The micelles exhibited excellent thermal stability. In-situ SAXS profiles of a 16 wt % 1CW-dC16-PEG2K solution heated from 25° C. to 85° C. are shown in FIG. 20B. The peptide helicity reduces from 74%-55%, but the headgroup remains mainly helical (FIG. 27). The inter-particle distance decreases during heating, due, more than likely, to an increase in micelle concentration arising from the water condensation on the capillary wall during the heating process. The scattering profiles for q>0.08 Å$^{-1}$ confirmed the formation of well-defined micelles even at elevated temperatures. The micelles also exhibited exceptional long-term stability with no storage requirements. The SAXS profile of micelle solution remained the same after storing for 2 months at room temperature (FIG. 28). In the case of dC16-1CW-P2K-HHH micelles can still be clearly seen after 9 months (FIG. 29).

The stability of micelles was further studied using Förster resonant energy transfer (FRET) to quantify cargo leakage. A lipophilic FRET pair, 3,3'-dioctadecyloxacarbocyanine perchlorate (DiO, donor) and 1,1'-dioctadecyl-3,3,3',3'-tetramethylindocarbocyanine perchlorate (DiI, acceptor), were independently sequestered in 1CW-dC16-PEG2K micelles. Minimal fluorescence due to energy transfer was seen and essentially no cargo leakage was observed after over 44 hrs of mixing at room temperature, consistent with the extremely slow kinetics of subunit exchange (FIG. 20C).

Figure 20:
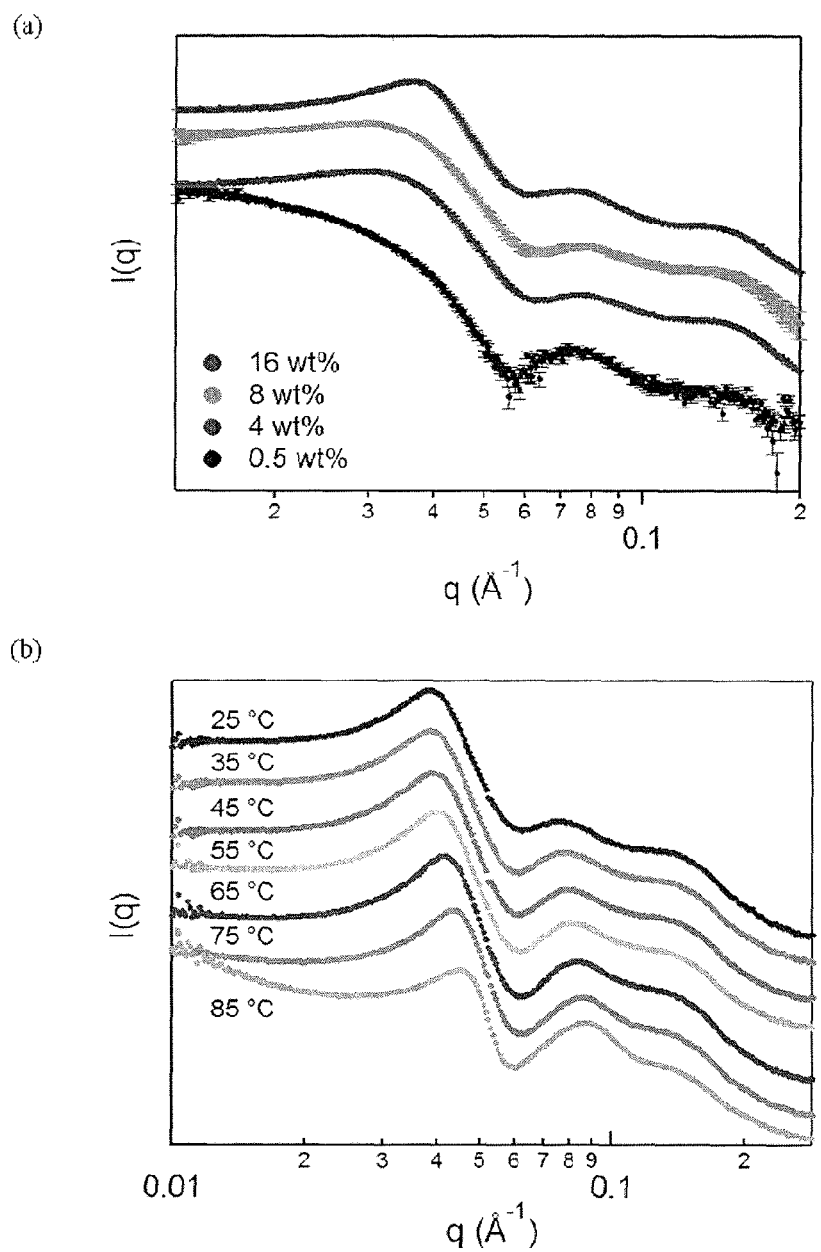
FIG. 20 shows the thermal stability of the micelles.
Figure 20:
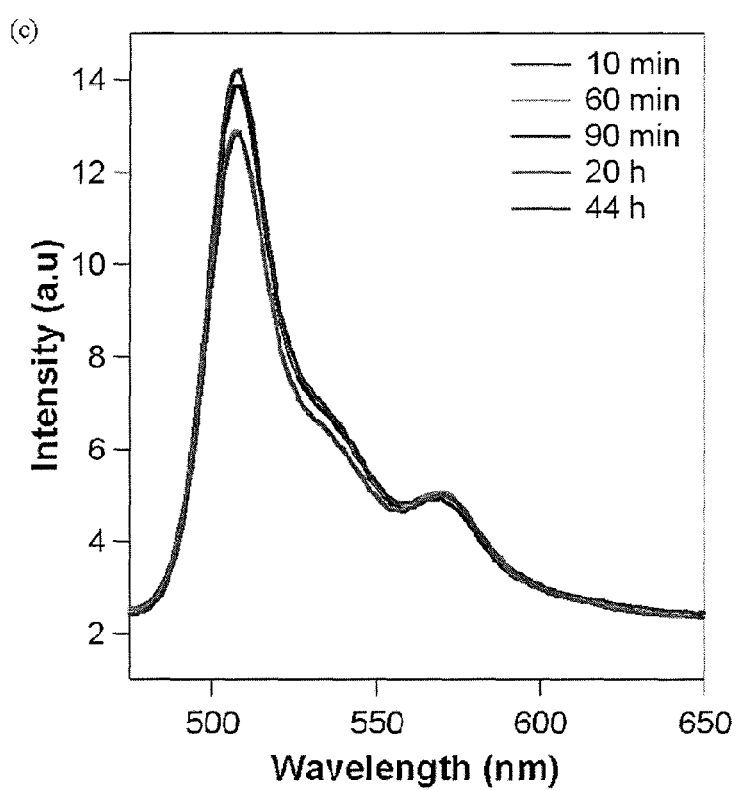
Figure 21:
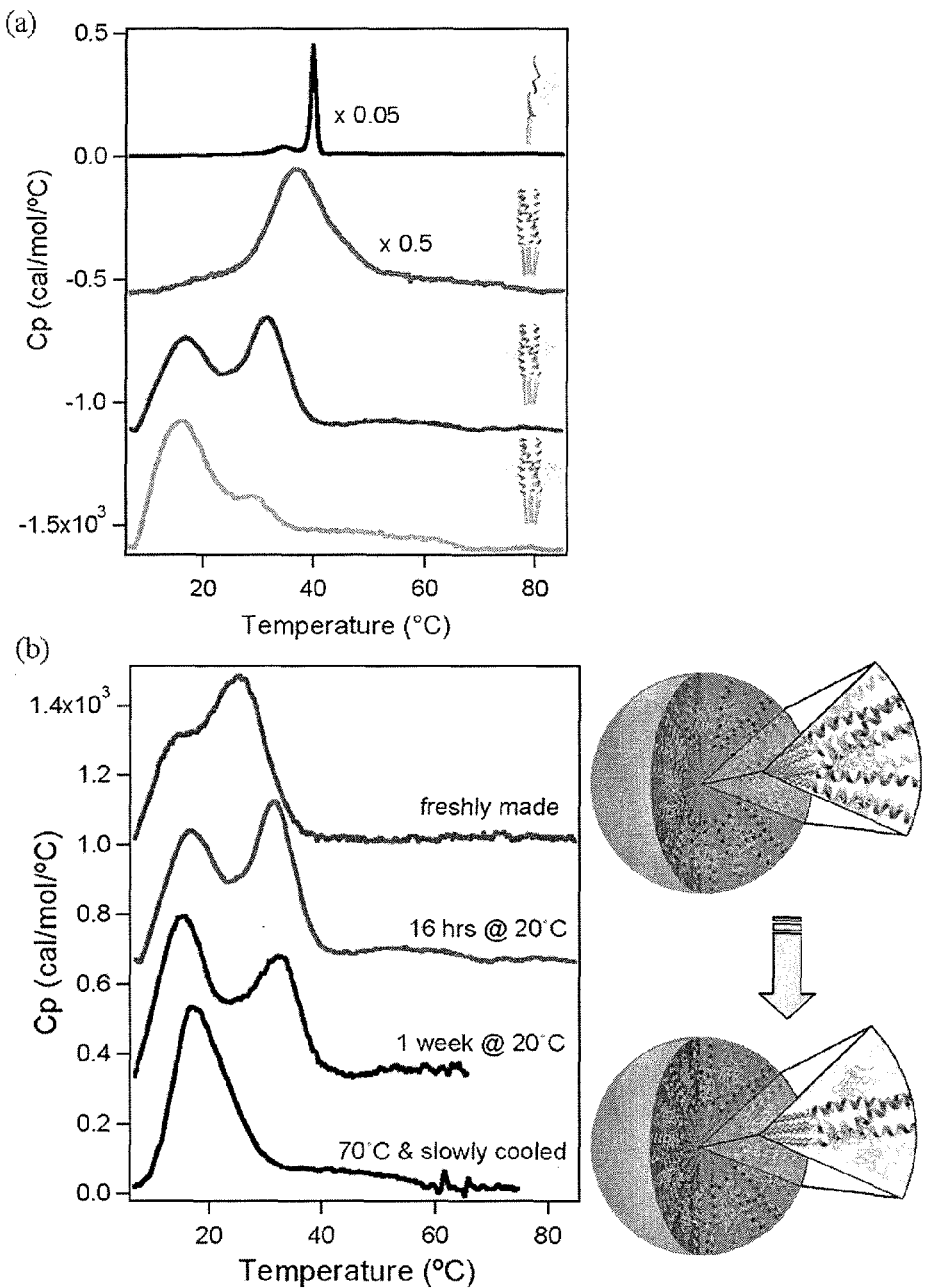
FIG. 21 shows the differential scanning calorimetry (DSC) curves for the peptide amphiphiles based on peptide-polymer conjugates.
Figure 30:
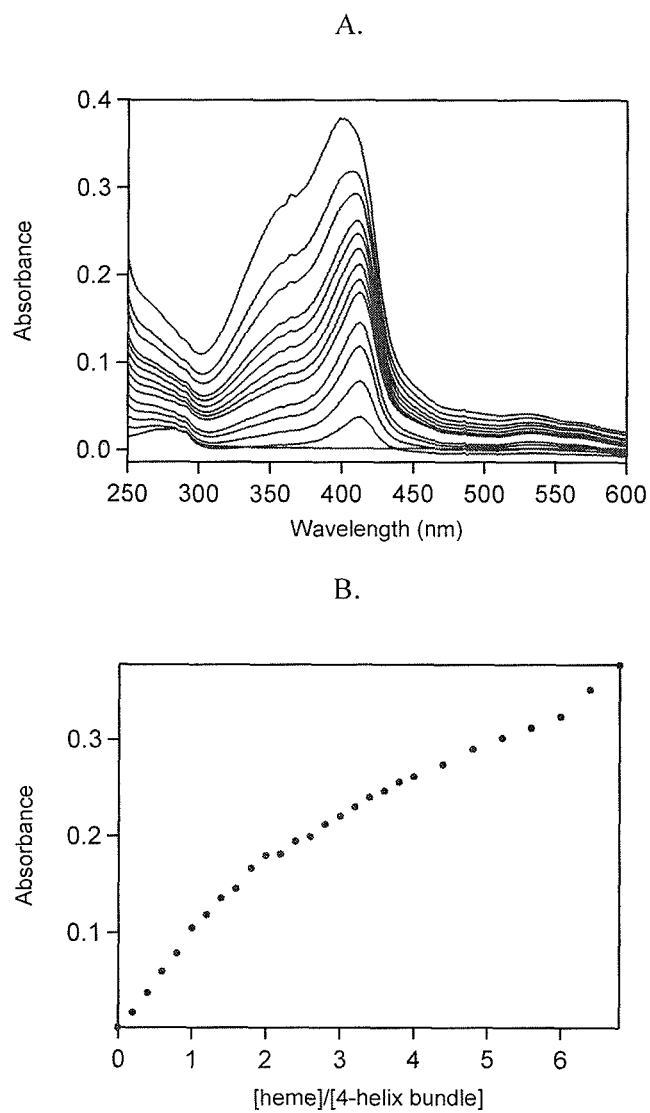
FIG. 30 shows the tertiary structure of the peptide is retained upon self-assembly of the amphiphiles to form micelle.
Figure 31:
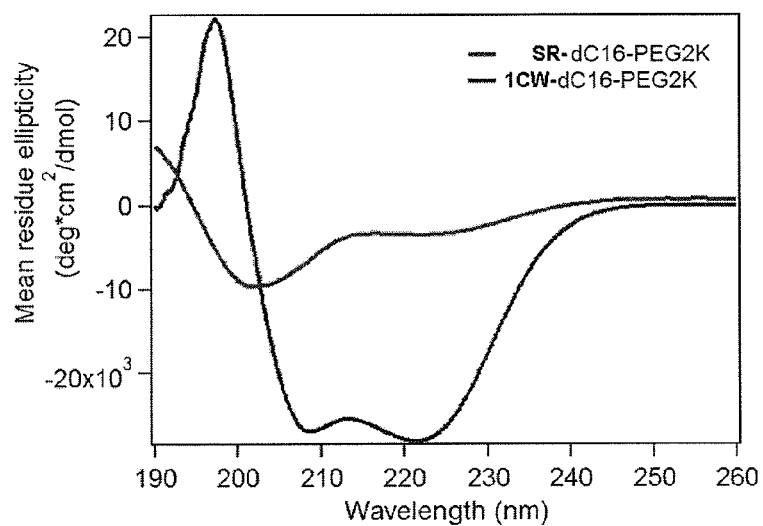
FIG. 31 shows the circular dichroism spectra of SR-dC16-PEG2K conjugate 14 (top on right) and 1CW-dC16-PEGK conjugate 16 (bottom on right). SR-dC16-PEG2K forms predominantly a random coil, with a helical content of less than 5%, as compared to 1CW-dC16-PEG2K, which has a helical content of 74% under the same conditions.

The alkyl packing of the lipid moiety in the hydrophobic core of the nanoparticles reflects the ordered organization of helical peptides of the headgroups. FIG. 21A shows the differential scanning calorimetry (DSC) curves for SR-dC16-PEG2K, 1CW-dC16, 1 CW-dC16-P2K and 1CW-dC16-P5K upon heating from 5° C. to 85° C. All solutions were incubated at 20° C. for 16 hrs before the DSC measurements. A sharp endothermic peak with a melting temperature of 42° C. can be seen for SR-dC16-PEG2K and conjugating PEG to the side chain of a random coil does not compromise the ordering of the alkyl chain. However, this is not the case for designed amphiphiles based on helical peptide-polymer conjugates. Two broad peaks centered at 17 and 32° C. were observed for 1CW-dC16-P2K and mainly one peak centered at 17° C. was seen for 1CW-dC16-P5K when the molecular weight of conjugated PEG increases to 5000 Da. Correlation of DSC results with fluorescence self-quenching results indicate that the exception stability of nanoparticles is achieved mainly through the headgroup packing leading to significant repulsion energy stored within nanoparticles, although this is realized with the sacrifice of lipid chain packing.

dC16-1CW-PEG2K is based on a peptide that self-associates to form 3-helix bundle. Upon dissolving, the peptide folds into a helix instantaneously and a fraction of peptides form helix bundles during micelle formation. As shown in FIG. 30, this was confirmed by the heme-titration results of H10H24-dC16-PEG2K that forms micelles, ~12 nm in diameter. Over time, the peptides form helix bundles via a lateral diffusion. FIG. 21 shows the DSC scans of solutions of 1cw-dC16-PEG2K that were freshly made, incubated at 20° C. for 16 hrs and 1 week, and heated to 70° C. and slowly cooled down, respectively. The endothermal peak centered at 17° C. intensifies with longer incubation and corresponds to 1CW-dC16-PEG2K forming 3-helix bundle. This self-association process of the headgroup is slow for 1CW-dC16-PEG2K due to the crystallization of alkyl chains in the core and can be accelerated by heating the solution to 70° C., after which only one peak at 17° C. is seen as shown in FIG. 20. For 1CW-dC16-PEG5K, longer PEG chain leads to a higher lateral pressure that splays the alkyl chains and the headgroups arrange locally to form 3-helix bundles during the incubation at 20° C.

Figure 22:
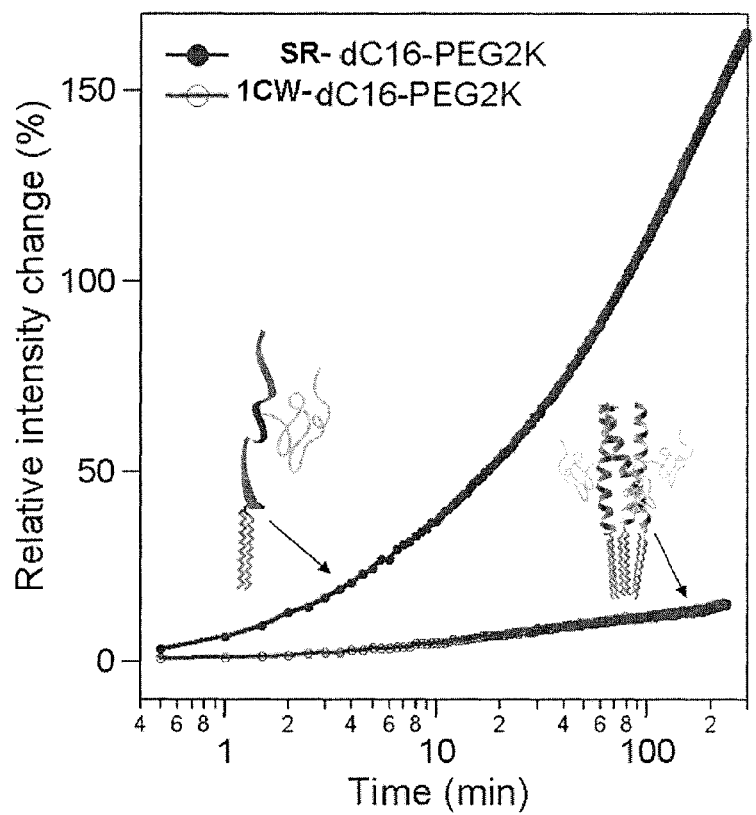
FIG. 22 shows the time dependence of the fluorescence recovery of fluorescein labeled nanoparticles upon the addition of non-labeled nanoparticles. SR-dC16-PEG2K refers to conjugate 14 in Table 1, and 1CW-dC16-PEG2K refers to conjugate 16 in Table 1.

Without being bound to any particular theory, the stability of the micelles is believed to arise from conjugation of PEG chains to the exterior of the helix bundle. With PEG conjugation, all micelle solutions appear to be stable for days, in contrast to 1CW-dC16 that forms large precipitates within a few hours. To delineate the effects of protein structure, the kinetics of subunit exchange was studied by monitoring the fluorescence recovery of a self-quenching fluorophore, fluorescein, which was attached to the peptide C-terminus. Fluorescein-labeled nanoparticles (donor) were prepared at a concentration of 16 μM in 25 mM phosphate buffer at pH 7.4. Non-labeled nanoparticles (acceptor) were prepared at a concentration of 3.6 mM using the same buffer. The two solutions were mixed in a 11:1 volume ratio, giving a donor:acceptor molar ratio of 1:40. Time dependent fluorescence intensity was recorded every 30 seconds upon mixing, with the excitation wavelength at 488 nm and emission at 515 nm. Mixing preformed labeled nanoparticles with non-labeled nanoparticles will result in fluorescence recovery to varying degree depending on the kinetics of subunit desorption from pre-existing nanoparticles. It was determined that even though the hydrophobic core is mainly disordered, micelles of 1CW-dC16-PEG2K exhibit much slower subunit exchange kinetics than that of SR-dC16-PEG2K (FIG. 22). This is strong evidence that it is the PEG springs that stabilize micelles. The present studies show that upon micelle formation, helical peptides determine the position of PEG chains both radially and laterally in a micelle and confine the PEG chains to enhance entropic repulsion.

Although the foregoing invention has been described in some detail by way of illustration and example for purposes of clarity of understanding, one of skill in the art will appreciate that certain changes and modifications may be practiced within the scope of the appended claims. In addition, each reference provided herein is incorporated by reference in its entirety to the same extent as if each reference was individually incorporated by reference. Where a conflict exists between the instant application and a reference provided herein, the instant application shall dominate.

```
Sequences
                                    SEQ ID NO: 1
         EVEALEKKVAALECKVQALEKKVEALEHGW

SEQ ID NO: 2
         GGGEIWKLHEEFLCKFEELLKLHEERLKKM

SEQ ID NO: 3
         AYSSGAPPMPPF

SEQ ID NO: 4
         EGKAGEKAGAALKCGVQELEKGAEAGEGGW

SEQ ID NO: 5
         EVEALEKKVAALESKVQALEKKVEALEHGW
```

What is claimed is:

1. A conjugate comprising:
a helix bundle-forming helical peptide selected from the group consisting of SEQ ID NO: 1, SEQ ID NO: 2, and SEQ ID NO: 5;
a first polymer covalently linked to the helical peptide, wherein the first polymer is linked to the helical peptide at an amino acid other than the N- or C-terminus; and
a hydrophobic moiety covalently linked to the N-terminus of the helical peptide, wherein the hydrophobic moiety comprises a second polymer or a lipid moiety comprising from 1 to 6 $C_{10-20}$ alkyl groups.

2. The conjugate of claim 1, wherein the first polymer is a hydrophilic polymer.

3. The conjugate of claim 1, wherein the first polymer is polyethyleneglycol.

4. The conjugate of claim 1, wherein the second polymer comprises polybutadiene.

5. The conjugate of claim 1, wherein the lipid moiety comprises 1, 2 or 4 $C_{10-20}$ alkyl groups.

6. The conjugate of claim 1, further comprising an amino acid residue covalently linked to the C-terminus of the helix bundle-forming helical peptide.

7. The conjugate of claim 6, wherein the amino acid residue comprises a member selected from the group consisting of GGG, HHH, KK, EE, RGD, and AYSSGAPPMPPF (SEQ ID NO: 3).

8. The conjugate of claim 1, wherein
the helix bundle-forming helical peptide comprises SEQ ID NO: 1;
the first polymer comprises polyethylene glycol;
the hydrophobic moiety comprises the lipid moiety which comprises lysine and two $C_{16}$ alkyl chains; and
an amino acid residue of from 2 to about 20 amino acids, covalently linked to the C-terminus of the peptide.

9. A helix bundle comprising from 2 to 6 conjugates of claim 1.

10. The helix bundle of claim 9, comprising 3 conjugates.

11. The helix bundle of claim 9, comprising 4 conjugates.

12. A particle comprising from about 20 to about 200 conjugates of claim 1.

13. The particle of claim 12, further comprising at least one member selected from the group consisting of a therapeutic agent, a diagnostic agent, DNA, and an oligonucleotide.

14. A method of forming a particle of claim 12, the method comprising:
contacting a plurality of conjugates of claim 1 such that the conjugates self-assemble to form the particles of claim 12.

15. The method of claim 14, wherein the conjugates are at a concentration of from about 1 nM to about 1 M.

* * * * *